US009522954B2

(12) United States Patent
Wu et al.

(10) Patent No.: US 9,522,954 B2
(45) Date of Patent: Dec. 20, 2016

(54) ANTI-LRP5 ANTIBODIES AND METHODS OF USE

(71) Applicant: Genentech Inc., South San Francisco, CA (US)

(72) Inventors: Yan Wu, Foster City, CA (US); Weilan Ye, Foster City, CA (US); Jeremy Bryant Burton, Burlingame, CA (US); Cecilia Chiu, San Carlos, CA (US)

(73) Assignee: GENENTECH, INC., South San Francisco, CA (US)

( * ) Notice: Subject to any disclaimer, the term of this patent is extended or adjusted under 35 U.S.C. 154(b) by 0 days.

(21) Appl. No.: 14/879,702

(22) Filed: Oct. 9, 2015

(65) Prior Publication Data

US 2016/0185855 A1 Jun. 30, 2016

Related U.S. Application Data

(62) Division of application No. 13/744,766, filed on Jan. 18, 2013, now Pat. No. 9,200,072.

(60) Provisional application No. 61/588,100, filed on Jan. 18, 2012.

(51) Int. Cl.
| | |
|---|---|
| *C07H 21/04* | (2006.01) |
| *C07K 16/28* | (2006.01) |
| *A61K 39/395* | (2006.01) |
| *A61P 27/02* | (2006.01) |
| *A61K 39/00* | (2006.01) |

(52) U.S. Cl.
CPC ............. *C07K 16/28* (2013.01); *A61K 39/395* (2013.01); *C07H 21/04* (2013.01); *A61K 2039/505* (2013.01); *C07K 2317/75* (2013.01); *C07K 2317/92* (2013.01)

(58) Field of Classification Search
None
See application file for complete search history.

(56) References Cited

U.S. PATENT DOCUMENTS

2010/0129375 A1   5/2010   Junge et al.

FOREIGN PATENT DOCUMENTS

| WO | 2009/036338 A2 | 3/2009 |
|---|---|---|
| WO | 2010/030813 | 3/2010 |

OTHER PUBLICATIONS

Almagro et al., "Humanization of antibodies" Frontiers in Bioscience 13:1619-1633 (Jan. 2008).
Baron et al., "Targeting the Wnt/beta-catenin pathway to regulate bone formation in the adult skeleton" Endocrinology 148(6):2635-43 ( 2007).
Berger et al., "Isolation of a candidate gene for Norrie disease by positional cloning" Nat Genet 1(3):199-203 (Jun. 1992).
Bjorkland et al., "The Internally Truncated LRP5 Receptor Presents a Therapeutic Target in Breast Cancer", PLoS One 4(1):e4243 ( 2009).
Casset et al., "A peptide mimetic of an anti-CD4 monoclonal antibody by rational design" Biochem Bioph Res Co 307(1):198-205 (Jul. 18, 2003).
Chen et al., "Isolation and characterization of a candidate gene for Norrie disease" Nat Genet 1(3):204-8 (Jun. 1992).
Chen et el., "Selection and analysis of an optimized anti-VERF antibody: Crystal structure of an affinity-matured Fab in complex with antigen" J Mol Biol 293:865-881 ( 1999).
Chothia et al., "Canonical structures for the hypervariable regions of immunoglobulins" J Mol Biol 196:901-917 ( 1987).
De Pascalis et al., "Grafting of 'abbreviated' complementarity-determining regions containing specificity-determining residues essential for ligand contact to engineer a less immunogenic humanized monoclonal antibody" J Immunol 169:3076-3084 ( 2002).
Ettenberg et al., "Inhibition of Tumorigenesis Driven by Different Wnt Proteins Requires Blockade of Distinct Ligand-Binding Regions by LPR6 Antibodies" PNAS 107(35):15473-15478 ( 2010).
Gallop et al., "Applications of Combinatorial Technologies to Drug Discovery Background and peptide combinatorial libraries" J Med Chem 37(9):1233-1251 (Apr. 29, 1994).
Gong et al., "Wnt Isoform-Specific Internactions with Coreceptor Specify Inhibition or Potentiation of Signaling by LPR6 Antibodies" PLos One 5(9):e12682 ( 2010).
Holm et al., "Functional mapping and single chain construction of the anti-cytokeratin 8 monoclonal antibody TS1" Molecular Immunology 44:1075-1084 ( 2007).
International Preliminary Report on Patentability PCT/US2013/022045, Date of Issuance Jul. 22, 014.
International Search Report PCT/US2013/022045, mailed Aug. 4, 2013, pp. 3.
Junge et al., "TSPAN12 regulates retinal vascular development by promoting Norrin- but not Wnt-induced FZD4/beta-catenin singaling" Cell 139(2):299-311 ( 2009).
Lee et al., "Bivalent antibody phage display mimics natural immunoglobulin" J Immunol Methods 284:119-132 ( 2004).
Liang et al., "Function blocking antibodies to neuropilin-1 generated from a design human synthetic antibody phage library" J. Mol. Biol. 366:815-829 ( 2007).
MacCallum et al., "Antibody-antigen Interactions: Contact Analysis and Binding Site Topography" Journal of Molecular Biology 262:732-746 ( 1996).
Poulter et al., "Mutations in TSPAN12 cause autosomal-dominant familial exudative vitreoretinopathy" Am J Hum Genet. 86(2):248-53 (Feb. 12, 2010).
Poulter et al., "Recessive mutations in TSPAN12 cause retinal dysplasia and severe familial exudative vitreoretinopahty (FEVR)" Invest Ophthalmol Vis Sci. 53(6):2873-9 (May 14, 2012).
Rey et al., "Wnt Modulators in the Biotech Pipeline" Dev. Dyn. 239(1):102-114 ( 2010).
Robitaille et al., "Mutant frizzled-4 disrupts retinal angiogenesis in familial exudative vitreoretinopathy" Nat Genet 32(2):326-30 (Sep. 2002).
Rudikoff et al., "Single amino acid substitution alteringantigen-binding specificity," Proc. Nat. Acad. Sci. USA, vol. 79, pp. 1979-1983, Mar. 1982.

(Continued)

*Primary Examiner* — Zachary Howard
(74) *Attorney, Agent, or Firm* — Frank Jn Berendt

(57) ABSTRACT

The invention provides anti-LRP5 antibodies and methods of making and using the same.

31 Claims, 11 Drawing Sheets

(56) References Cited

OTHER PUBLICATIONS

Toomes et al., "Mutations in LRP5 and FZD4 underlie the common familial exudative vitreoretinopathy locus on chromosome 11q" Am J Hum Genet 74(4):721-30 ( 2004).
Vajdos et al., "Comprehensive Functional Maps of the Antigen-binding Site of an Anti-ErbB2 Antibody Obtained with Shotgun Scanning Mutagenesis" Journal of Molecular Biology 320:415-428 ( 2002).
Wei et al., "The LDL Receptor-Related Protein LPR6 Mediates Internalization of Lethality of Anthrax Toxin" Cell 124:1141-1154 ( 2006).
Wu et al., "Humanization of a murine monoclonal antibody by simultaneous optimization of framework and CDR residues" J Mol Biol 294(1):151-162 (Nov. 19, 1999).
Xu et al., "Vascular Development in the Retina and Inner Ear: Control by Norrin and Frizzled-4 a High-Affinity Ligand-Receptor Pair" Cell 116:883-895 ( 2004).
Yang et al., "Novel TSPAN12 mutations in patients with familial exudative vitreoretinopathy and their associated phenotypes" Mol Vis. 17:1128-35 (Apr. 29, 2011).

LRP5 Antibody, P6C.42, Partially Rescues Vascular Defects in the TSpan12 Knockout Mice *in vivo*.

LRP5 Antibody, P6C.42, Partially Rescues Vascular Defects in the TSpan12 Knockout Mice *in vivo*.

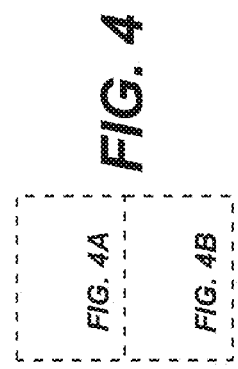

| Kabat# | 41 42 43 44 45 46 47 48 49 50 51 52 A B C 53 54 55 56 57 58 59 60 61 62 63 64 65 66 67 68 69 70 71 72 73 74 75 76 77 78 |
|---|---|
| | Kabat - CDR H2 |
| | Chothia - CDR H2 |
| | Contact - CDR H2 |
| YW629.42    | P G K G L E W V G A I S G S G G S T Y Y A D S V K G R F T I S R D N S K N T L |
| YW629.42.57 | P G K G L E W V A I S H G S G G S T Y Y A D S V K G R F T I S R D N S K N T L |
| YW629.42.58 | P G K G L E W V G I I H G S P W S T Y Y A D S V K G R F T I S R D N S K N T L |
| YW629.42.65 | P G K G L E W V G A I G G S P G S T Y Y A D S V K G R F T I S R D N S K N T L |
| YW629.51    | P G K G L E W V G S I R H S G G N S Y Y A D S V K G R F T I S R D N S K N T L |
| YW629.51.13 | P G K G L E W V G S I R H S G G N T Y Y A D S V K G R F T I S R D N S K N T L |
| YW629.51.61 | P G K G L E W V G S I R H S G G N S Y Y A D S V K G R F T I S R D N S K N T L |
| YW629.51.63 | P G K G L E W V G S I R H S G G N S Y Y A D S V K G R F T I S R D N S K N T L |
| YW629.51.77 | P G K G L E W V G S I R H S G G T S Y Y A D S V K G R F T I S R D N S K N T L |
| YW629.51.78 | P G K G L E W V G S I R H S G G N T Y Y A D S V K G R F T I S R D N S K N T L |
| YW629.51.80 | P G K G L E W V G S I R H S G G N A Y Y A D S V K G R F T I S R D N S K N T L |

| Kabat# | 79 80 81 82 A B C 83 84 85 86 87 88 89 90 91 92 93 94 95 96 97 98 99 100 A B C D E F G B 101 102 103 104 105 106 |
|---|---|
| | Kabat - CDR H3 |
| | Chothia - CDR H3 |
| | Contact - CDR H3 |
| YW629.42    | Y L Q M N S L R A E D T A V Y Y C A R Y Y R Y A P Y R S L G M D V W G Q G |
| YW629.42.57 | Y L Q M N S L R A E D T A V Y Y C A R Y Y R Y A P Y R S L G M D V W G Q G |
| YW629.42.58 | Y L Q M N S L R A E D T A V Y Y C A R Y Y R Y A P Y R S L G M D V W G Q G |
| YW629.42.65 | Y L Q M N S L R A E D T A V Y Y C A R Y Y R Y A P Y R S L G M D V W G Q G |
| YW629.51    | Y L Q M N S L R A E D T A V Y Y C A R W I P Q S S F A S Y K S G F D Y W G Q G |
| YW629.51.13 | Y L Q M N S L R A E D T A V Y Y C A R W I P Q S S F R S Y K S G F D Y W G Q G |
| YW629.51.61 | Y L Q M N S L R A E D T A V Y Y C A R W I P Q S S F F A S Y K S G F D Y W G Q G |
| YW629.51.63 | Y L Q M N S L R A E D T A V Y Y C A R W I P Q S S F F A S Y K S G F D Y W G Q G |
| YW629.51.77 | Y L Q M N S L R A E D T A V Y Y C A R W I P Q S S F F A S Y K S G F D Y W G Q G |
| YW629.51.78 | Y L Q M N S L R A E D T A V Y Y C A R W I P Q S S F F A S Y K S G F D Y W G Q G |
| YW629.51.80 | Y L Q M N S L R A E D T A V Y Y C A R W I P Q S S F F A S Y K S G F D Y W G Q G |

| Kabat# | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 | 32 | 33 | 34 | 35 | 36 | 37 |
|---|---|---|---|---|---|---|---|---|---|---|---|---|---|---|---|---|---|---|---|---|---|---|---|---|---|---|---|---|---|---|---|---|---|---|---|---|---|
| | | | | | | | | | | | | | | | | | | | | | | | | Kabat - CDR L1 | | | | | | | | | | | | | |
| | | | | | | | | | | | | | | | | | | | | | | | | Chothia - CDR L1 | | | | | | | | | | | | | |
| | | | | | | | | | | | | | | | | | | | | | | | | | | | | | | Contact - CDR L1 | | | | | | |
| YW629.42 | D | I | Q | M | T | Q | S | P | S | S | L | S | A | S | V | G | D | R | V | T | I | T | C | R | A | S | Q | G | I | S | S | Y | L | A | W | Y | Q |
| YW629.42.57 | D | I | Q | M | T | Q | S | P | S | S | L | S | A | S | V | G | D | R | V | T | I | T | C | R | A | S | Q | G | I | S | S | Y | L | A | W | Y | Q |
| YW629.42.58 | D | I | Q | M | T | Q | S | P | S | S | L | S | A | S | V | G | D | R | V | T | I | T | C | R | A | S | Q | G | I | S | S | Y | L | A | W | Y | Q |
| YW629.42.65 | D | I | Q | M | T | Q | S | P | S | S | L | S | A | S | V | G | D | R | V | T | I | T | C | R | A | S | Q | G | I | S | S | Y | L | A | W | Y | Q |
| YW629.51 | D | I | Q | M | T | Q | S | P | S | S | L | S | A | S | V | G | D | R | V | T | I | T | C | R | A | S | Q | G | I | S | S | Y | L | A | W | Y | Q |
| YW629.51.13 | D | I | Q | M | T | Q | S | P | S | S | L | S | A | S | V | G | D | R | V | T | I | T | C | R | A | S | Q | V | M | G | Y | Y | L | A | W | Y | Q |
| YW629.51.61 | D | I | Q | M | T | Q | S | P | S | S | L | S | A | S | V | G | D | R | V | T | I | T | C | R | A | S | Q | S | I | Y | Y | Y | L | A | W | Y | Q |
| YW629.51.63 | D | I | Q | M | T | Q | S | P | S | S | L | S | A | S | V | G | D | R | V | T | I | T | C | R | A | S | Q | V | I | F | G | Y | L | A | W | Y | Q |
| YW629.51.77 | D | I | Q | M | T | Q | S | P | S | S | L | S | A | S | V | G | D | R | V | T | I | T | C | R | A | S | Q | G | I | F | Y | Y | L | A | W | Y | Q |
| YW629.51.78 | D | I | Q | M | T | Q | S | P | S | S | L | S | A | S | V | G | D | R | V | T | I | T | C | R | A | S | Q | A | I | Y | S | Y | L | A | W | Y | Q |
| YW629.51.80 | D | I | Q | M | T | Q | S | P | S | S | L | S | A | S | V | G | D | R | V | T | I | T | C | R | A | S | Q | G | I | S | S | Y | L | A | W | Y | Q |

SEQUENCE LISTING

<160> NUMBER OF SEQ ID NOS: 60

<210> SEQ ID NO 1
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Gly Ala Ile Ser Ser Ser Gly Ser Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Tyr Arg Tyr Ala Pro Tyr Arg Ser Leu Gly Met Asp Val
            100                 105                 110

Trp Gly Gln
        115

<210> SEQ ID NO 2
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Gly Ala Ile Ser Ala Pro Gly Ser Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Tyr Arg Tyr Ala Pro Tyr Arg Ser Leu Gly Met Asp Val
            100                 105                 110

Trp Gly Gln
        115

<210> SEQ ID NO 3
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Gly Ala Ile Ser Ser Pro Gly Trp Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Tyr Arg Tyr Ala Pro Tyr Arg Ser Leu Gly Met Asp Val
            100                 105                 110

Trp Gly Gln
        115

```
<210> SEQ ID NO 4
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Gly Gly Ile Ser Ser Pro Gly Ser Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Tyr Arg Tyr Ala Pro Tyr Arg Ser Leu Gly Met Asp Val
            100                 105                 110

Trp Gly Gln
        115

<210> SEQ ID NO 5
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ser Arg Ile Ser Ser Asn Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Trp Ile Pro Gln Ser Tyr Pro Phe Ala Ser Tyr Lys Ser Gly
            100                 105                 110

Phe Asp Tyr Trp Gly Gln
        115

<210> SEQ ID NO 6
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 6

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ser Arg Ile Ser Ser Asn Gly Gly Ser Thr Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Arg Trp Ile Pro Gln Ser Tyr Pro Phe Arg Ser Tyr Lys Ser Gly
            100                 105                 110

Phe Asp Tyr Trp Gly Gln
        115

<210> SEQ ID NO 7
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ser Arg Ile Ser Ser Asn Gly Gly Ser Thr Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Arg Trp Ile Pro Gln Ser Tyr Pro Phe Ala Ser Tyr Lys Ser Gly
            100                 105                 110

Phe Asp Tyr Trp Gly Gln
        115

<210> SEQ ID NO 8
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

```
Ala Met His Trp Val Arg Gln Ala Pro Gly Lys Gly Leu Glu Trp Val
            35                  40                  45

Ser Arg Ile Ser Ser Asn Gly Gly Ser Thr Tyr Tyr Ala Asp Ser Val
 50                      55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg Trp Ile Pro Gln Ser Tyr Pro Phe Ala Ser Tyr Lys Ser Gly
            100                 105                 110

Phe Asp Tyr Trp Gly Gln
            115

<210> SEQ ID NO 9
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
            35                  40                  45

Ser Arg Ile Ser Ser Asn Gly Gly Ser Thr Tyr Tyr Ala Asp Ser Val
 50                      55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg Trp Ile Pro Gln Ser Tyr Pro Phe Ala Ser Tyr Lys Ser Gly
            100                 105                 110

Phe Asp Tyr Trp Gly Gln
            115

<210> SEQ ID NO 10
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
            35                  40                  45

Ser Arg Ile Ser Ser Asn Gly Gly Ser Thr Tyr Tyr Ala Asp Ser Val
 50                      55                  60

Lys Gly Arg Phe Thr Ile Ser Arg Asp Asn Ser Lys Asn Thr Leu Tyr
 65                  70                  75                  80
```

```
Leu Gln Met Asn Ser Leu Arg Ala Glu Asp Thr Ala Val Tyr Tyr Cys
                85                  90                  95

Ala Arg Trp Ile Pro Gln Ser Tyr Pro Phe Ala Ser Tyr Lys Ser Gly
            100                 105                 110

Phe Asp Tyr Trp Gly Gln
        115

<210> SEQ ID NO 11
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ser Arg Ile Ser Ser Asn Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Trp Ile Pro Gln Ser Tyr Pro Phe Ala Ser Tyr Lys Ser Gly
            100                 105                 110

Phe Asp Tyr Trp Gly Gln
        115

<210> SEQ ID NO 12
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Tyr
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ser Tyr Pro Phe
                85                  90                  95

Thr Phe Gly Gln Gly Thr Lys Val Glu Ile Lys Arg
            100                 105
```

```
<210> SEQ ID NO 13
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Tyr
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ser Tyr Pro Phe
                85                  90                  95

Thr Phe Gly Gln Gly Thr Lys Val Glu Ile Lys Arg
            100                 105

<210> SEQ ID NO 14
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Tyr
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ser Tyr Pro Phe
                85                  90                  95

Thr Phe Gly Gln Gly Thr Lys Val Glu Ile Lys Arg
            100                 105

<210> SEQ ID NO 15
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Tyr
            20                  25                  30
```

```
Leu Ala Trp Tyr Gln Gln Lys Pro Gly Lys Ala Pro Lys Leu Leu Ile
         35                  40                  45

Tyr Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Tyr Leu Tyr Pro Phe
                 85                  90                  95

Thr Phe Gly Gln Gly Thr Lys Val Glu Ile Lys Arg
            100                 105
```

<210> SEQ ID NO 16
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Ser Ser Tyr
             20                  25                  30

Leu Ala Trp Tyr Gln Gln Lys Pro Gly Lys Ala Pro Lys Leu Leu Ile
         35                  40                  45

Tyr Asp Ala Ser Ser Leu Glu Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Tyr Ser Tyr Pro Phe
                 85                  90                  95

Thr Phe Gly Gln Gly Thr Lys Val Glu Ile Lys Arg
            100                 105
```

<210> SEQ ID NO 17
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Ser Ser Tyr
             20                  25                  30

Leu Ala Trp Tyr Gln Gln Lys Pro Gly Lys Ala Pro Lys Leu Leu Ile
         35                  40                  45

Tyr Asp Ala Ser Ser Leu Glu Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Tyr Ser Tyr Pro Phe
                 85                  90                  95

Thr Phe Gly Gln Gly Thr Lys Val Glu Ile Lys Arg
            100                 105
```

```
<210> SEQ ID NO 18
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Val Met Gly Tyr Tyr
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ser Tyr Pro Phe
                85                  90                  95

Thr Phe Gly Gln Gly Thr Lys Val Glu Ile Lys Arg
            100                 105

<210> SEQ ID NO 19
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Tyr Tyr Tyr
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ser Tyr Pro Phe
                85                  90                  95

Thr Phe Gly Gln Gly Thr Lys Val Glu Ile Lys Arg
            100                 105

<210> SEQ ID NO 20
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Val Ile Tyr Gly Tyr
            20                  25                  30
```

```
Leu Ala Trp Tyr Gln Gln Lys Pro Gly Lys Ala Pro Lys Leu Leu Ile
         35                  40                  45

Tyr Asp Ala Ser Thr Arg Glu Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Tyr Ser Tyr Pro Phe
                 85                  90                  95

Thr Phe Gly Gln Gly Thr Lys Val Glu Ile Lys Arg
            100                 105

<210> SEQ ID NO 21
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Phe Tyr Tyr
             20                  25                  30

Leu Ala Trp Tyr Gln Gln Lys Pro Gly Lys Ala Pro Lys Leu Leu Ile
         35                  40                  45

Tyr Asp Ala Ser Thr Leu Glu Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Tyr Ser Tyr Pro Phe
                 85                  90                  95

Thr Phe Gly Gln Gly Thr Lys Val Glu Ile Lys Arg
            100                 105

<210> SEQ ID NO 22
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ala Ile Tyr Ser Tyr
             20                  25                  30

Leu Ala Trp Tyr Gln Gln Lys Pro Gly Lys Ala Pro Lys Leu Leu Ile
         35                  40                  45

Tyr Asp Ala Ser Ser Leu Glu Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Tyr Ser Tyr Pro Phe
                 85                  90                  95

Thr Phe Gly Gln Gly Thr Lys Val Glu Ile Lys Arg
            100                 105
```

```
<210> SEQ ID NO 23
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Tyr Tyr Arg Tyr Ala Pro Tyr Arg Ser Leu Gly Met Asp Val
1               5                   10

<210> SEQ ID NO 24
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: Ala or Arg

<400> SEQUENCE: 24

Trp Ile Pro Gln Ser Tyr Pro Phe Xaa Ser Tyr Lys Ser Gly Phe Asp
1               5                   10                  15

Tyr

<210> SEQ ID NO 25
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Leu or Ser

<400> SEQUENCE: 25

Gln Gln Tyr Tyr Xaa Tyr Pro Phe Thr
1               5

<210> SEQ ID NO 26
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Ala or Gly
<220> FEATURE:
<221> NAME/KEY: MOD_RES
<222> LOCATION: (5)..(5)
<223> OTHER INFORMATION: Ala or Ser
<220> FEATURE:
<221> NAME/KEY: MOD_RES
<222> LOCATION: (6)..(6)
<223> OTHER INFORMATION: Pro or Ser
<220> FEATURE:
<221> NAME/KEY: MOD_RES
<222> LOCATION: (8)..(8)
<223> OTHER INFORMATION: Ser or Trp
```

```
<400> SEQUENCE: 26

Gly Xaa Ile Ser Xaa Xaa Gly Xaa Ser Thr Tyr Tyr Ala Asp Ser Val
1               5                   10                  15

Lys Gly

<210> SEQ ID NO 27
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Ser Arg Ile Ser Ser Asn Gly Gly Ser Thr Tyr Tyr Ala Asp Ser Val
1               5                   10                  15

Lys Gly

<210> SEQ ID NO 28
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: His or Ser

<400> SEQUENCE: 28

Gly Phe Thr Phe Ser Ser Tyr Ala Met Xaa
1               5                   10

<210> SEQ ID NO 29
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Arg Ala Ser Gln Gly Ile Ser Ser Tyr Leu Ala
1               5                   10

<210> SEQ ID NO 30
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Ala, Gly, Ser or Val
<220> FEATURE:
<221> NAME/KEY: MOD_RES
<222> LOCATION: (6)..(6)
<223> OTHER INFORMATION: Ile or Met
<220> FEATURE:
<221> NAME/KEY: MOD_RES
<222> LOCATION: (7)..(7)
<223> OTHER INFORMATION: Phe, Gly, Ser or Tyr
<220> FEATURE:
<221> NAME/KEY: MOD_RES
<222> LOCATION: (8)..(8)
<223> OTHER INFORMATION: Gly, Ser or Tyr
```

```
<400> SEQUENCE: 30

Arg Ala Ser Gln Xaa Xaa Xaa Xaa Tyr Leu Ala
1               5                   10

<210> SEQ ID NO 31
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Ala Ala Ser Ser Leu Gln Ser
1               5

<210> SEQ ID NO 32
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Ser or Thr
<220> FEATURE:
<221> NAME/KEY: MOD_RES
<222> LOCATION: (5)..(5)
<223> OTHER INFORMATION: Leu or Arg

<400> SEQUENCE: 32

Asp Ala Ser Xaa Xaa Glu Ser
1               5

<210> SEQ ID NO 33
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Leu or Ser

<400> SEQUENCE: 33

Gln Gln Tyr Tyr Xaa Tyr Pro Phe Thr
1               5

<210> SEQ ID NO 34
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25
```

```
<210> SEQ ID NO 35
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Trp Val Arg Gln Ala Pro Gly Lys Gly Leu Glu Trp Val
1               5                   10

<210> SEQ ID NO 36
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ala Arg
                20                  25                  30

<210> SEQ ID NO 37
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Trp Gly Gln
1

<210> SEQ ID NO 38
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Asp Ile Gln Met Thr Gln Ser Pro Ser Ser Leu Ser Ala Ser Val Gly
1               5                   10                  15

Asp Arg Val Thr Ile Thr Cys
                20

<210> SEQ ID NO 39
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Trp Tyr Gln Gln Lys Pro Gly Lys Ala Pro Lys Leu Leu Ile Tyr
1               5                   10                  15
```

-continued

<210> SEQ ID NO 40
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 41
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Phe Gly Gln Gly Thr Lys Val Glu Ile Lys Arg
1               5                   10

<210> SEQ ID NO 42
<211> LENGTH: 1615
<212> TYPE: PRT
<213> ORGANISM: Homo sapiens

<400> SEQUENCE: 42

Met Glu Ala Ala Pro Gly Pro Pro Trp Pro Leu Leu Leu Leu Leu Leu
1               5                   10                  15

Leu Leu Leu Ala Leu Cys Gly Cys Pro Ala Pro Ala Ala Ala Ala Ser
            20                  25                  30

Pro Leu Leu Leu Phe Ala Asn Arg Arg Asp Val Arg Leu Val Asp Ala
        35                  40                  45

Gly Gly Val Lys Leu Glu Ser Thr Ile Val Val Ser Gly Leu Glu Asp
    50                  55                  60

Ala Ala Ala Val Asp Phe Gln Phe Ser Lys Gly Ala Val Tyr Trp Thr
65                  70                  75                  80

Asp Val Ser Glu Glu Ala Ile Lys Gln Thr Tyr Leu Asn Gln Thr Gly
                85                  90                  95

Ala Ala Val Gln Asn Val Val Ile Ser Gly Leu Val Ser Pro Asp Gly
            100                 105                 110

Leu Ala Cys Asp Trp Val Gly Lys Lys Leu Tyr Trp Thr Asp Ser Glu
        115                 120                 125

Thr Asn Arg Ile Glu Val Ala Asn Leu Asn Gly Thr Ser Arg Lys Val
    130                 135                 140

Leu Phe Trp Gln Asp Leu Asp Gln Pro Arg Ala Ile Ala Leu Asp Pro
145                 150                 155                 160

Ala His Gly Tyr Met Tyr Trp Thr Asp Trp Gly Glu Thr Pro Arg Ile
                165                 170                 175

Glu Arg Ala Gly Met Asp Gly Ser Thr Arg Lys Ile Ile Val Asp Ser
            180                 185                 190

Asp Ile Tyr Trp Pro Asn Gly Leu Thr Ile Asp Leu Glu Glu Gln Lys
        195                 200                 205

Leu Tyr Trp Ala Asp Ala Lys Leu Ser Phe Ile His Arg Ala Asn Leu
    210                 215                 220

```
Asp Gly Ser Phe Arg Gln Lys Val Val Glu Gly Ser Leu Thr His Pro
225                 230                 235                 240

Phe Ala Leu Thr Leu Ser Gly Asp Thr Leu Tyr Trp Thr Asp Trp Gln
            245                 250                 255

Thr Arg Ser Ile His Ala Cys Asn Lys Arg Thr Gly Gly Lys Arg Lys
        260                 265                 270

Glu Ile Leu Ser Ala Leu Tyr Ser Pro Met Asp Ile Gln Val Leu Ser
    275                 280                 285

Gln Glu Arg Gln Pro Phe Phe His Thr Arg Cys Glu Glu Asp Asn Gly
290                 295                 300

Gly Cys Ser His Leu Cys Leu Leu Ser Pro Ser Glu Pro Phe Tyr Thr
305                 310                 315                 320

Cys Ala Cys Pro Thr Gly Val Gln Leu Gln Asp Asn Gly Arg Thr Cys
                325                 330                 335

Lys Ala Gly Ala Glu Glu Val Leu Leu Leu Ala Arg Arg Thr Asp Leu
            340                 345                 350

Arg Arg Ile Ser Leu Asp Thr Pro Asp Phe Thr Asp Ile Val Leu Gln
        355                 360                 365

Val Asp Asp Ile Arg His Ala Ile Ala Ile Asp Tyr Asp Pro Leu Glu
370                 375                 380

Gly Tyr Val Tyr Trp Thr Asp Asp Glu Val Arg Ala Ile Arg Arg Ala
385                 390                 395                 400

Tyr Leu Asp Gly Ser Gly Ala Gln Thr Leu Val Asn Thr Glu Ile Asn
                405                 410                 415

Asp Pro Asp Gly Ile Ala Val Asp Trp Val Ala Arg Asn Leu Tyr Trp
            420                 425                 430

Thr Asp Thr Gly Thr Asp Arg Ile Glu Val Thr Arg Leu Asn Gly Thr
        435                 440                 445

Ser Arg Lys Ile Leu Val Ser Glu Asp Leu Asp Glu Pro Arg Ala Ile
    450                 455                 460

Ala Leu His Pro Val Met Gly Leu Met Tyr Trp Thr Asp Trp Gly Glu
465                 470                 475                 480

Asn Pro Lys Ile Glu Cys Ala Asn Leu Asp Gly Gln Glu Arg Arg Val
                485                 490                 495

Leu Val Asn Ala Ser Leu Gly Trp Pro Asn Gly Leu Ala Leu Asp Leu
            500                 505                 510

Gln Glu Gly Lys Leu Tyr Trp Gly Asp Ala Lys Thr Asp Lys Ile Glu
        515                 520                 525

Val Ile Asn Val Asp Gly Thr Lys Arg Arg Thr Leu Leu Glu Asp Lys
    530                 535                 540

Leu Pro His Ile Phe Gly Phe Thr Leu Leu Gly Asp Phe Ile Tyr Trp
545                 550                 555                 560

Thr Asp Trp Gln Arg Arg Ser Ile Glu Arg Val His Lys Val Lys Ala
                565                 570                 575

Ser Arg Asp Val Ile Ile Asp Gln Leu Pro Asp Leu Met Gly Leu Lys
            580                 585                 590

Ala Val Asn Val Ala Lys Val Val Gly Thr Asn Pro Cys Ala Asp Arg
        595                 600                 605

Asn Gly Gly Cys Ser His Leu Cys Phe Phe Thr Pro His Ala Thr Arg
    610                 615                 620

Cys Gly Cys Pro Ile Gly Leu Glu Leu Leu Ser Asp Met Lys Thr Cys
625                 630                 635                 640
```

-continued

```
Ile Val Pro Glu Ala Phe Leu Val Phe Thr Ser Arg Ala Ala Ile His
                645                 650                 655

Arg Ile Ser Leu Glu Thr Asn Asn Asn Asp Val Ala Ile Pro Leu Thr
            660                 665                 670

Gly Val Lys Glu Ala Ser Ala Leu Asp Phe Asp Val Ser Asn Asn His
        675                 680                 685

Ile Tyr Trp Thr Asp Val Ser Leu Lys Thr Ile Ser Arg Ala Phe Met
690                 695                 700

Asn Gly Ser Ser Val Glu His Val Val Glu Phe Gly Leu Asp Tyr Pro
705                 710                 715                 720

Glu Gly Met Ala Val Asp Trp Met Gly Lys Asn Leu Tyr Trp Ala Asp
                725                 730                 735

Thr Gly Thr Asn Arg Ile Glu Val Ala Arg Leu Asp Gly Gln Phe Arg
            740                 745                 750

Gln Val Leu Val Trp Arg Asp Leu Asp Asn Pro Arg Ser Leu Ala Leu
        755                 760                 765

Asp Pro Thr Lys Gly Tyr Ile Tyr Trp Thr Glu Trp Gly Gly Lys Pro
770                 775                 780

Arg Ile Val Arg Ala Phe Met Asp Gly Thr Asn Cys Met Thr Leu Val
785                 790                 795                 800

Asp Lys Val Gly Arg Ala Asn Asp Leu Thr Ile Asp Tyr Ala Asp Gln
                805                 810                 815

Arg Leu Tyr Trp Thr Asp Leu Asp Thr Asn Met Ile Glu Ser Ser Asn
            820                 825                 830

Met Leu Gly Gln Glu Arg Val Val Ile Ala Asp Asp Leu Pro His Pro
        835                 840                 845

Phe Gly Leu Thr Gln Tyr Ser Asp Tyr Ile Tyr Trp Thr Asp Trp Asn
850                 855                 860

Leu His Ser Ile Glu Arg Ala Asp Lys Thr Ser Gly Arg Asn Arg Thr
865                 870                 875                 880

Leu Ile Gln Gly His Leu Asp Phe Val Met Asp Ile Leu Val Phe His
                885                 890                 895

Ser Ser Arg Gln Asp Gly Leu Asn Asp Cys Met His Asn Asn Gly Gln
            900                 905                 910

Cys Gly Gln Leu Cys Leu Ala Ile Pro Gly Gly His Arg Cys Gly Cys
        915                 920                 925

Ala Ser His Tyr Thr Leu Asp Pro Ser Ser Arg Asn Cys Ser Pro Pro
930                 935                 940

Thr Thr Phe Leu Leu Phe Ser Gln Lys Ser Ala Ile Ser Arg Met Ile
945                 950                 955                 960

Pro Asp Asp Gln His Ser Pro Asp Leu Ile Leu Pro Leu His Gly Leu
                965                 970                 975

Arg Asn Val Lys Ala Ile Asp Tyr Asp Pro Leu Asp Lys Phe Ile Tyr
            980                 985                 990

Trp Val Asp Gly Arg Gln Asn Ile Lys Arg Ala Lys Asp Asp Gly Thr
        995                 1000                1005

Gln Pro Phe Val Leu Thr Ser Leu Ser Gln Gly Gln Asn Pro Asp
        1010                1015                1020

Arg Gln Pro His Asp Leu Ser Ile Asp Ile Tyr Ser Arg Thr Leu
        1025                1030                1035

Phe Trp Thr Cys Glu Ala Thr Asn Thr Ile Asn Val His Arg Leu
        1040                1045                1050
```

-continued

```
Ser Gly Glu Ala Met Gly Val Val Leu Arg Gly Asp Arg Asp Lys
    1055                1060                1065

Pro Arg Ala Ile Val Val Asn Ala Glu Arg Gly Tyr Leu Tyr Phe
    1070                1075                1080

Thr Asn Met Gln Asp Arg Ala Ala Lys Ile Glu Arg Ala Ala Leu
    1085                1090                1095

Asp Gly Thr Glu Arg Glu Val Leu Phe Thr Thr Gly Leu Ile Arg
    1100                1105                1110

Pro Val Ala Leu Val Val Asp Asn Thr Leu Gly Lys Leu Phe Trp
    1115                1120                1125

Val Asp Ala Asp Leu Lys Arg Ile Glu Ser Cys Asp Leu Ser Gly
    1130                1135                1140

Ala Asn Arg Leu Thr Leu Glu Asp Ala Asn Ile Val Gln Pro Leu
    1145                1150                1155

Gly Leu Thr Ile Leu Gly Lys His Leu Tyr Trp Ile Asp Arg Gln
    1160                1165                1170

Gln Gln Met Ile Glu Arg Val Glu Lys Thr Thr Gly Asp Lys Arg
    1175                1180                1185

Thr Arg Ile Gln Gly Arg Val Ala His Leu Thr Gly Ile His Ala
    1190                1195                1200

Val Glu Glu Val Ser Leu Glu Glu Phe Ser Ala His Pro Cys Ala
    1205                1210                1215

Arg Asp Asn Gly Gly Cys Ser His Ile Cys Ile Ala Lys Gly Asp
    1220                1225                1230

Gly Thr Pro Arg Cys Ser Cys Pro Val His Leu Val Leu Leu Gln
    1235                1240                1245

Asn Leu Leu Thr Cys Gly Glu Pro Pro Thr Cys Ser Pro Asp Gln
    1250                1255                1260

Phe Ala Cys Ala Thr Gly Glu Ile Asp Cys Ile Pro Gly Ala Trp
    1265                1270                1275

Arg Cys Asp Gly Phe Pro Glu Cys Asp Asp Gln Ser Asp Glu Glu
    1280                1285                1290

Gly Cys Pro Val Cys Ser Ala Ala Gln Phe Pro Cys Ala Arg Gly
    1295                1300                1305

Gln Cys Val Asp Leu Arg Leu Arg Cys Asp Gly Glu Ala Asp Cys
    1310                1315                1320

Gln Asp Arg Ser Asp Glu Ala Asp Cys Asp Ala Ile Cys Leu Pro
    1325                1330                1335

Asn Gln Phe Arg Cys Ala Ser Gly Gln Cys Val Leu Ile Lys Gln
    1340                1345                1350

Gln Cys Asp Ser Phe Pro Asp Cys Ile Asp Gly Ser Asp Glu Leu
    1355                1360                1365

Met Cys Glu Ile Thr Lys Pro Pro Ser Asp Asp Ser Pro Ala His
    1370                1375                1380

Ser Ser Ala Ile Gly Pro Val Ile Gly Ile Ile Leu Ser Leu Phe
    1385                1390                1395

Val Met Gly Gly Val Tyr Phe Val Cys Gln Arg Val Val Cys Gln
    1400                1405                1410

Arg Tyr Ala Gly Ala Asn Gly Pro Phe Pro His Glu Tyr Val Ser
    1415                1420                1425

Gly Thr Pro His Val Pro Leu Asn Phe Ile Ala Pro Gly Gly Ser
    1430                1435                1440
```

```
Gln His Gly Pro Phe Thr Gly Ile Ala Cys Gly Lys Ser Met Met
    1445                1450                1455

Ser Ser Val Ser Leu Met Gly Gly Arg Gly Gly Val Pro Leu Tyr
    1460                1465                1470

Asp Arg Asn His Val Thr Gly Ala Ser Ser Ser Ser Ser Ser Ser
    1475                1480                1485

Thr Lys Ala Thr Leu Tyr Pro Pro Ile Leu Asn Pro Pro Pro Ser
    1490                1495                1500

Pro Ala Thr Asp Pro Ser Leu Tyr Asn Met Asp Met Phe Tyr Ser
    1505                1510                1515

Ser Asn Ile Pro Ala Thr Ala Arg Pro Tyr Arg Pro Tyr Ile Ile
    1520                1525                1530

Arg Gly Met Ala Pro Pro Thr Thr Pro Cys Ser Thr Asp Val Cys
    1535                1540                1545

Asp Ser Asp Tyr Ser Ala Ser Arg Trp Lys Ala Ser Lys Tyr Tyr
    1550                1555                1560

Leu Asp Leu Asn Ser Asp Ser Asp Pro Tyr Pro Pro Pro Pro Thr
    1565                1570                1575

Pro His Ser Gln Tyr Leu Ser Ala Glu Asp Ser Cys Pro Pro Ser
    1580                1585                1590

Pro Ala Thr Glu Arg Ser Tyr Phe His Leu Phe Pro Pro Pro Pro
    1595                1600                1605

Ser Pro Cys Thr Asp Ser Ser
    1610                1615

<210> SEQ ID NO 43
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Gly Phe Thr Phe Ser Ser Tyr Ala Met His
1               5                   10

<210> SEQ ID NO 44
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Trp Ile Pro Gln Ser Tyr Pro Phe Ala Ser Tyr Lys Ser Gly Phe Asp
1               5                   10                  15

Tyr

<210> SEQ ID NO 45
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Arg Ala Ser Gln Val Met Gly Tyr Tyr Leu Ala
1               5                   10
```

```
<210> SEQ ID NO 46
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Asp Ala Ser Ser Leu Glu Ser
1               5

<210> SEQ ID NO 47
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Gln Gln Tyr Tyr Ser Tyr Pro Phe Thr
1               5

<210> SEQ ID NO 48
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Gly Phe Thr Phe Ser Ser Tyr Ala Met Ser
1               5                   10

<210> SEQ ID NO 49
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Gly Ala Ile Ser Ser Ser Gly Ser Ser Thr Tyr Tyr Ala Asp Ser Val
1               5                   10                  15

Lys Gly

<210> SEQ ID NO 50
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Gly Ala Ile Ser Ala Pro Gly Ser Ser Thr Tyr Tyr Ala Asp Ser Val
1               5                   10                  15

Lys Gly

<210> SEQ ID NO 51
<211> LENGTH: 18
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 51

Gly Ala Ile Ser Ser Pro Gly Trp Ser Thr Tyr Tyr Ala Asp Ser Val
1               5                   10                  15

Lys Gly

<210> SEQ ID NO 52
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Gly Gly Ile Ser Ser Pro Gly Ser Ser Thr Tyr Tyr Ala Asp Ser Val
1               5                   10                  15

Lys Gly

<210> SEQ ID NO 53
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Gln Gln Tyr Tyr Leu Tyr Pro Phe Thr
1               5

<210> SEQ ID NO 54
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Trp Ile Pro Gln Ser Tyr Pro Phe Arg Ser Tyr Lys Ser Gly Phe Asp
1               5                   10                  15

Tyr

<210> SEQ ID NO 55
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Arg Ala Ser Gln Ser Ile Tyr Tyr Tyr Leu Ala
1               5                   10

<210> SEQ ID NO 56
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 56

Arg Ala Ser Gln Val Ile Tyr Gly Tyr Leu Ala
1               5                   10

<210> SEQ ID NO 57
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Asp Ala Ser Thr Arg Glu Ser
1               5

<210> SEQ ID NO 58
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Arg Ala Ser Gln Gly Ile Phe Tyr Tyr Leu Ala
1               5                   10

<210> SEQ ID NO 59
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Asp Ala Ser Thr Leu Glu Ser
1               5

<210> SEQ ID NO 60
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Arg Ala Ser Gln Ala Ile Tyr Ser Tyr Leu Ala
1               5                   10
```

ANTI-LRP5 ANTIBODIES AND METHODS OF USE

CROSS REFERENCE TO RELATED APPLICATIONS

This application is a Divisional of U.S. patent application Ser. No. 13/744,766, filed on Jan. 18, 2013, and which claims benefit under 35 U.S.C. 119 to U.S. Provisional Application No. 61/588,100, filed on Jan. 18, 2012, the entire contents of which are incorporated herein by reference.

This application contains a Sequence Listing submitted via EFS-Web and hereby incorporated by reference in its entirety. Said ASCII copy, created on Oct. 8, 2015, is named P04855-US-2_SequenceListing.txt and is 44,971 bytes in size.

FIELD OF THE INVENTION

The present invention relates to anti-LRP5 antibodies and methods of using the same.

BACKGROUND

It is now well established that angiogenesis is an important contributor to the pathogenesis of a variety of disorders. These include solid tumors and metastasis, intraocular neovascular diseases such as retinopathies, e.g., diabetic retinopathy, retinal vein occlusion (RVO), wet age-related macular degeneration (AMD), neovascular glaucoma, immune rejection of transplanted corneal tissue and other tissues, and rheumatoid arthritis. Duda et al. J. Clin. Oncology 25(26): 4033-42 (2007); Kesisis et al. Curr. Pharm. Des. 13: 2795-809 (2007); Zhang & Ma Prog. Ret. & Eye Res. 26: 1-37 (2007).

The retina receives its blood supply from retinal vessels, which supply the inner part of the retina, and choroidal vessels, which supply the outer part. Damage to retinal vessels occurs in several disease processes including diabetic retinopathy, retinopathy of prematurity, and central and branched retinal vein occlusions (ischemic retinopathies). Retinal ischemia from this damage results in undesirable neovascularization. Choroidal neovascularization occurs in a number of other disease processes, including AMD. In contrast, incomplete vascularization of the retina is a hallmark in patients with certain genetic diseases, e.g. familial exudative vitreoretinopathy (FEVR), Coats' disease, and Norrie disease caused by mutation of the Wnt receptor Frizzled4 (Fzd4), the co-receptor LRP5 or the secreted ligand Norrin (Berger et al. Nature Genet. 1:199-203 (1992); Chen et al. Nature Genet. 1:204-208 (1992); Robitaille et al. Nature Genet. 32:326-30 (2002); Toomes et al. Am. J. Hum. Genet. 74:721-30 (2004)). An additional protein, TSPAN12, has been shown to be involved in Norrin signaling (Junge et al. Cell 139:299-311 (2009) and WO 2010/030813). Mutations in the Tspan12 gene are also reported to be causal for FEVR (Poulter et al. Invest Ophthalmol Vis Sci. 14; 53(6): 2873-9 (2012); Yang et al. Molecular Vision 17:1128-1135 (2011); Poulter et al. The American Journal of Human Genetics 86, 248-253 (2010)). Models for these genetic diseases are available in mice knocked out for the corresponding homologous genes.

Despite the many advances in the field of ocular angiogenesis, there remains a need to identify targets and develop means that can supplement or enhance the efficacy of existing therapies.

SUMMARY

The invention provides anti-LRP5 antibodies and methods of making and using the same, particularly in the treatment of conditions and diseases associated with angiogenesis.

In one aspect, the invention provides an isolated antibody that binds to Low-density lipoprotein receptor-related protein 5 (LRP5), wherein the antibody potentiates Norrin activity and/or Norrin/Fzd4 signaling. In some embodiments, the antibody is a monoclonal antibody. In some embodiments the antibody is a human, humanized, or chimeric antibody. In some embodiments, the antibody is an antibody fragment that binds LRP5.

In some embodiments, the antibody comprises (a) HVR-H3 comprising the amino acid sequence YYRYAPYRSLGMDV (SEQ ID NO: 23) or WIPQSYPFX$_1$SYKSGFDY, wherein X$_1$ is A or R (SEQ ID NO: 24), (b) HVR-L3 comprising the amino acid sequence QQYYX$_1$YPFT, wherein X$_1$ is L or S (SEQ ID NO: 25), and (c) HVR-H2 comprising the amino acid sequence GX$_1$ISX$_2$X$_3$GX$_4$STYYADSVKG, wherein X$_1$ is A or G, X$_2$ is A or S, X$_3$ is P or S, X$_4$ is S or W (SEQ ID NO: 26), or SRISSNGGSTYYADSVKG (SEQ ID NO: 27). In some embodiments, the antibody comprises (a) HVR-H1 comprising the amino acid sequence GFTFSSYAMX$_1$, wherein X$_1$ is H or S (SEQ ID NO: 28), (b) HVR-H2 comprising the amino acid sequence GX$_1$ISX$_2$X$_3$GX$_4$STYYADSVKG, wherein X$_1$ is A or G, X$_2$ is A or S, X$_3$ is P or S, X$_4$ is S or W (SEQ ID NO: 26), or SRISSNGGSTYYADSVKG (SEQ ID NO: 27) and (c) HVR-H3 comprising the amino acid sequence YYRYAPYRSLGMDV (SEQ ID NO: 23) or WIPQSYPFX$_1$SYKSGFDY, wherein X$_1$ is A or R (SEQ ID NO: 24). In some embodiments, the antibody further comprises (a) HVR-L1 comprising the amino acid sequence RASQGISSYLA (SEQ ID NO: 29) or RASQX$_1$X$_2$X$_3$X$_4$YLA, wherein X$_1$ is A, G, S or V, X$_2$ is I or M, X$_3$ is F, G, S or Y, and X$_4$ is G, S or Y (SEQ ID NO: 30); (b) HVR-L2 comprising the amino acid sequence AASSLQS (SEQ ID NO: 31) or DASX$_1$X$_2$ES, wherein X$_1$ is S or T and X$_2$ is L or R (SEQ ID NO: 32); and (c) HVR-L3 comprising the amino acid sequence QQYYX$_1$YPFT, wherein X$_1$ is L or S (SEQ ID NO: 33). In some embodiments, the antibody comprises (a) HVR-L1 comprising the amino acid sequence RASQGISSYLA (SEQ ID NO: 29) or RASQX$_1$X$_2$X$_3$X$_4$YLA, wherein X$_1$ is A, G, S or V, X$_2$ is I or M, X$_3$ is G, F, Y or S, and X$_4$ is G, Y or S (SEQ ID NO: 30); (b) HVR-L2 comprising the amino acid sequence AASSLQS (SEQ ID NO: 31) or DASX$_1$X$_2$ES, wherein X$_1$ is S or T and X$_2$ is L or R (SEQ ID NO: 32); and (c) HVR-L3 comprising the amino acid sequence QQYYX$_1$YPFT, wherein X$_1$ is L or S (SEQ ID NO: 33). In some embodiments, the antibody comprises one or more heavy chain variable domain framework sequences selected from the group consisting of SEQ ID NO: 34-37. In some embodiments, the antibody comprises (a) a VH sequence having at least 95% sequence identity to the amino acid sequence of one of SEQ ID NOs: 1 to 11; (b) a VL sequence having at least 95% sequence identity to the amino acid sequence of one of SEQ ID NOs: 12 to 22; or (c) a VH sequence as in (a) and a VL sequence as in (b). In some embodiments, the antibody comprises a VH sequence of one of SEQ ID NOs: 1 to 11. In some embodiments, the antibody comprises a VL sequence of one of SEQ ID NOs: 12 to 22. In some embodiments, the antibody comprises a VH sequence of one of SEQ ID NOs: 1 to 11 and a VL sequence of one of SEQ ID NOs: 12 to 22. In some embodiments, the antibody comprises the VH and VL sequences of an antibody show in FIGS. 4 and 5. In some embodiments, the antibody is a full length IgG1 antibody.

In another aspect, the invention provides isolated nucleic acid encoding an antibody of the invention. In some embodiments, the invention provides a host cell comprising the nucleic acid of claim 15. In some embodiments, the invention provides a method of producing an antibody comprising culturing the host cell of claim 16 so that the antibody is produced. In some embodiments, the method further comprises recovering the antibody from the host cell.

In some embodiments, the invention provides an immunoconjugate comprising an antibody of the invention and a cytotoxic agent. In some embodiments, the invention provides a pharmaceutical formulation comprising an antibody of the invention and a pharmaceutically acceptable carrier. In some embodiments, the pharmaceutical formulation further comprises an additional therapeutic agent, e.g. a VEGF antagonist (including, e.g., an anti-VEGF antibody or antibody fragment, e.g. ranibizumab, a soluble VEGF receptor, e.g. aflibercept, or an aptamer, e.g. pegaptanib), a TSPAN12 agonist, plasmin, plasminogen, tissue plasminogen activator, a TNF-α inhibitor, and/or a steroid, e.g. triamcinolone or dexamethasone.

In some embodiments, the invention provides an antibody of the invention for use as a medicament. In some embodiments, the invention provides an antibody of the invention for use in treating a retinopathy including proliferative diabetic retinopathy, CNV, AMD, diabetic and other ischemia-related retinopathies, DME, pathological myopia, von Hippel-Lindau disease, histoplasmosis of the eye, CRVO, BRVO, corneal neovascularization, retinal neovascularization, ROP, FEVR, Coats' disease, Norrie Disease, OPPG (Osteoporosis-Pseudoglioma Syndrome), subconjunctival hemorrhage, or hypertensive retinopathy. In some embodiments, the invention provides an antibody of the invention for use in potentiating Norrin activity and/or Norrin/Fzd4 signaling. In some embodiments, the invention provides an antibody of the invention for use in the manufacture of a medicament. In some embodiments, the medicament is for treatment of a retinopathy including proliferative diabetic retinopathy, CNV, AMD, diabetic and other ischemia-related retinopathies, DME, pathological myopia, von Hippel-Lindau disease, histoplasmosis of the eye, CRVO, BRVO, corneal neovascularization, retinal neovascularization, ROP, FEVR, Coats' disease, Norrie Disease, OPPG (Osteoporosis-Pseudoglioma Syndrome), subconjunctival hemorrhage, or hypertensive retinopathy. In some embodiments, the medicament is for potentiating Norrin activity and/or Norrin/Fzd4 signaling.

In some embodiments, the invention provides a method of treating an individual having a retinopathy including proliferative diabetic retinopathy, CNV, AMD, diabetic and other ischemia-related retinopathies, DME, pathological myopia, von Hippel-Lindau disease, histoplasmosis of the eye, CRVO, BRVO, corneal neovascularization, retinal neovascularization, ROP, FEVR, Coats' disease, Norrie Disease, OPPG (Osteoporosis-Pseudoglioma Syndrome), subconjunctival hemorrhage, or hypertensive retinopathy comprising administering to the individual an effective amount of an antibody of the invention. In some embodiments, the method further comprises administering to the individual an effective amount of an additional therapeutic agent, e.g. a VEGF antagonist (including, e.g., an anti-VEGF antibody or antibody fragment, e.g. ranibizumab, a soluble VEGF receptor, e.g. aflibercept, or an aptamer, e.g. pegaptanib), a recombinant NORRIN protein, a TSPAN12 agonist, plasmin, plasminogen, tissue plasminogen activator, a TNF-α inhibitor, and/or a steroid, e.g. triamcinolone or dexamethasone. In some embodiments, the invention provides a method of potentiating Norrin activity and/or Norrin/Fzd4 signaling in an individual comprising administering to the individual an effective amount of an antibody of the invention to potentiate Norrin activity and/or Norrin/Fzd4 signaling. In some embodiments, the invention provides a method of rescuing a signaling defect in an individual caused by mutation in Norrin and/or Fzd4 comprising administering the antibody of claim 1.

BRIEF DESCRIPTION OF THE FIGURES

FIGS. 4A and 4B show the heavy chain variable region sequences for various anti-LRP5 antibodies with CDR-H1, CDR-H2, and CDR-H3 boxed. The corresponding SEQ ID NOs: for these sequences are as follows: YW629.42 (SEQ ID NO: 1), YW629.42.57 (SEQ ID NO: 2), YW629.42.58 (SEQ ID NO: 3), YW629.42.65 (SEQ ID NO: 4), YW629.51 (SEQ ID NO: 5), YW629.51.13 (SEQ ID NO: 6), YW629.51.61 (SEQ ID NO: 7), YW629.51.63 (SEQ ID NO: 8), YW629.51.77 (SEQ ID NO: 9), YW629.51.78 (SEQ ID NO: 10), and YW629.51.80 (SEQ ID NO: 11).

FIGS. 5A and 5B show the light chain variable region sequences for various anti-LRP5 antibodies with CDR-L1, CDR-L2, and CDR-L3 boxed. The corresponding SEQ ID NOs: for these sequences are as follows: YW629.42 (SEQ ID NO: 12), YW629.42.57 (SEQ ID NO: 13), YW629.42.58 (SEQ ID NO: 14), YW629.42.65 (SEQ ID NO: 15), YW629.51 (SEQ ID NO: 16), YW629.51.13 (SEQ ID NO: 17), YW629.51.61 (SEQ ID NO: 18), YW629.51.63 (SEQ ID NO: 19), YW629.51.77 (SEQ ID NO: 20), YW629.51.78 (SEQ ID NO: 21), and YW629.51.80 (SEQ ID NO: 22).

DETAILED DESCRIPTION OF EMBODIMENTS OF THE INVENTION

I. Definitions

Figure 1A:
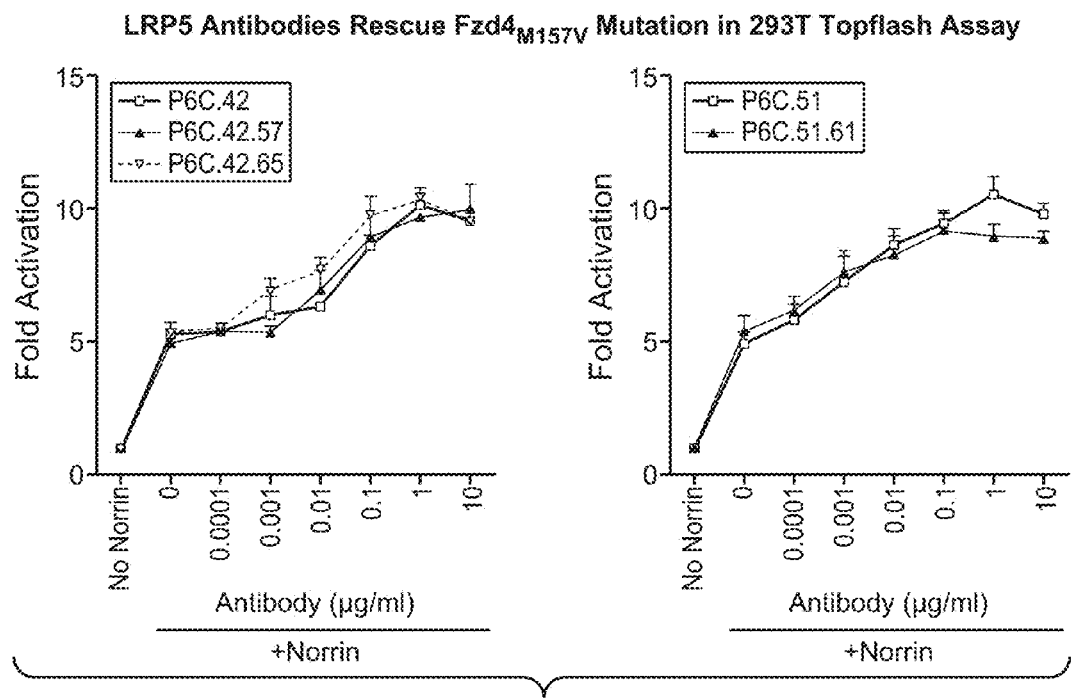
FIGS. 1A and 1B show that anti-LRP5 antibodies potentiate Norrin/Fzd4-mediated signaling and rescue $Fzd4_{M157V}$ mutation. In this Figure the prefix "P6C" is used, whereas in other places in the specification "YW629" is used interchangeably.

An "acceptor human framework" for the purposes herein is a framework comprising the amino acid sequence of a light chain variable domain (VL) framework or a heavy chain variable domain (VH) framework derived from a human immunoglobulin framework or a human consensus framework, as defined below. An acceptor human framework "derived from" a human immunoglobulin framework or a human consensus framework may comprise the same amino acid sequence thereof, or it may contain amino acid sequence changes. In some embodiments, the number of amino acid changes are 10 or less, 9 or less, 8 or less, 7 or less, 6 or less, 5 or less, 4 or less, 3 or less, or 2 or less. In some embodiments, the VL acceptor human framework is identical in sequence to the VL human immunoglobulin framework sequence or human consensus framework sequence.

"Affinity" refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein. Specific illustrative and exemplary embodiments for measuring binding affinity are described in the following.

An "affinity matured" antibody refers to an antibody with one or more alterations in one or more hypervariable regions (HVRs), compared to a parent antibody which does not possess such alterations, such alterations resulting in an improvement in the affinity of the antibody for antigen.

The terms "anti-LRP5 antibody" and "an antibody that binds to LRP5" refer to an antibody that is capable of binding LRP5 with sufficient affinity such that the antibody is useful as a diagnostic and/or therapeutic agent in targeting LRP5. In one embodiment, the extent of binding of an anti-LRP5 antibody to an unrelated, non-LRP5 protein is less than about 10% of the binding of the antibody to LRP5 as measured, e.g., by a radioimmunoassay (RIA). In certain embodiments, an antibody that binds to LRP5 has a dissociation constant (Kd) of ≤1 µM, ≤100 nM, ≤10 nM, ≤1 nM, ≤0.1 nM, ≤0.01 nM, or ≤0.001 nM (e.g. $10^{-8}$ M or less, e.g. from $10^{-8}$ M to $10^{-13}$ M, e.g., from $10^{-9}$ M to $10^{-13}$ M). In certain embodiments, an anti-LRP5 antibody binds to an epitope of LRP5 that is conserved among LRP5 from different species.

The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')$_2$; diabodies; linear antibodies; single-chain antibody molecules (e.g. scFv); and multispecific antibodies formed from antibody fragments.

An "antibody that binds to the same epitope" as a reference antibody refers to an antibody that blocks binding of the reference antibody to its antigen in a competition assay by 50% or more, and conversely, the reference antibody blocks binding of the antibody to its antigen in a competition assay by 50% or more. An exemplary competition assay is provided herein.

The term "chimeric" antibody refers to an antibody in which a portion of the heavy and/or light chain is derived from a particular source or species, while the remainder of the heavy and/or light chain is derived from a different source or species.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., IgG$_1$, IgG$_2$, IgG$_3$, IgG$_4$, IgA$_1$, and IgA$_2$. The heavy chain constant domains that correspond to the different classes of immunoglobulins are called α, δ, ε, γ, and µ, respectively.

The term "cytotoxic agent" as used herein refers to a substance that inhibits or prevents a cellular function and/or causes cell death or destruction. Cytotoxic agents include, but are not limited to radioactive isotopes (e.g., At$^{211}$, I$^{131}$, I$^{125}$, Y$^{90}$, Re$^{186}$, Re$^{188}$, Sm$^{153}$, Bi$^{212}$, P$^{32}$, Pb$^{212}$ and radioactive isotopes of Lu); chemotherapeutic agents or drugs (e.g., methotrexate, adriamicin, vinca alkaloids (vincristine, vinblastine, etoposide), doxorubicin, melphalan, mitomycin C, chlorambucil, daunorubicin or other intercalating agents); growth inhibitory agents; enzymes and fragments thereof such as nucleolytic enzymes; antibiotics; toxins such as small molecule toxins or enzymatically active toxins of bacterial, fungal, plant or animal origin, including fragments and/or variants thereof; and the various antitumor or anticancer agents disclosed below.

"Effector functions" refer to those biological activities attributable to the Fc region of an antibody, which vary with the antibody isotype. Examples of antibody effector functions include: C1q binding and complement dependent cytotoxicity (CDC); Fc receptor binding; antibody-dependent cell-mediated cytotoxicity (ADCC); phagocytosis; down regulation of cell surface receptors (e.g. B cell receptor); and B cell activation.

An "effective amount" of an agent, e.g., a pharmaceutical formulation, refers to an amount effective, at dosages and for periods of time necessary, to achieve the desired therapeutic or prophylactic result.

The term "Fc region" herein is used to define a C-terminal region of an immunoglobulin heavy chain that contains at least a portion of the constant region. The term includes native sequence Fc regions and variant Fc regions. In one embodiment, a human IgG heavy chain Fc region extends from Cys226, or from Pro230, to the carboxyl-terminus of the heavy chain. However, the C-terminal lysine (Lys447) of the Fc region may or may not be present. Unless otherwise specified herein, numbering of amino acid residues in the Fc region or constant region is according to the EU numbering system, also called the EU index, as described in Kabat et al., *Sequences of Proteins of Immunological Interest*, 5th Ed. Public Health Service, National Institutes of Health, Bethesda, Md., 1991.

"Framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1-H1(L1)-FR2-H2(L2)-FR3-H3(L3)-FR4.

The terms "full length antibody," "intact antibody," and "whole antibody" are used herein interchangeably to refer to an antibody having a structure substantially similar to a native antibody structure or having heavy chains that contain an Fc region as defined herein.

The terms "host cell," "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

A "human consensus framework" is a framework which represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al., *Sequences of Proteins of Immunological Interest*, Fifth Edition, NIH Publication 91-3242, Bethesda Md. (1991), vols. 1-3. In one embodiment, for the VL, the subgroup is subgroup kappa I as in Kabat et al., supra. In one embodiment, for the VH, the subgroup is subgroup III as in Kabat et al., supra.

A "humanized" antibody refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

The term "hypervariable region" or "HVR," as used herein, refers to each of the regions of an antibody variable domain which are hypervariable in sequence and/or form structurally defined loops ("hypervariable loops"). Generally, native four-chain antibodies comprise six HVRs; three in the VH (H1, H2, H3), and three in the VL (L1, L2, L3). HVRs generally comprise amino acid residues from the hypervariable loops and/or from the "complementarity determining regions" (CDRs), the latter being of highest sequence variability and/or involved in antigen recognition. Exemplary hypervariable loops occur at amino acid residues 26-32 (L1), 50-52 (L2), 91-96 (L3), 26-32 (H1), 53-55 (H2), and 96-101 (H3). (Chothia and Lesk, *J. Mol. Biol.* 196:901-917 (1987).) Exemplary CDRs (CDR-L1, CDR-L2, CDR-L3, CDR-H1, CDR-H2, and CDR-H3) occur at amino acid residues 24-34 of L1, 50-56 of L2, 89-97 of L3, 31-35B of H1, 50-65 of H2, and 95-102 of H3. (Kabat et al., *Sequences of Proteins of Immunological Interest*, 5th Ed. Public Health Service, National Institutes of Health, Bethesda, Md. (1991).) With the exception of CDR1 in VH, CDRs generally comprise the amino acid residues that form the hypervariable loops. CDRs also comprise "specificity determining residues," or "SDRs," which are residues that contact antigen. SDRs are contained within regions of the CDRs called abbreviated-CDRs, or a-CDRs. Exemplary a-CDRs (a-CDR-L1, a-CDR-L2, a-CDR-L3, a-CDR-H1, a-CDR-H2, and a-CDR-H3) occur at amino acid residues 31-34 of L1, 50-55 of L2, 89-96 of L3, 31-35B of H1, 50-58 of H2, and 95-102 of H3. (See Almagro and Fransson, *Front. Biosci.* 13:1619-1633 (2008).) Unless otherwise indicated, HVR residues and other residues in the variable domain (e.g., FR residues) are numbered herein according to Kabat et al., supra.

An "immunoconjugate" is an antibody conjugated to one or more heterologous molecule(s), including but not limited to a cytotoxic agent.

An "individual" or "subject" is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the individual or subject is a human.

An "isolated" antibody is one which has been separated from a component of its natural environment. In some embodiments, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC). For review of methods for assessment of antibody purity, see, e.g., Flatman et al., *J. Chromatogr. B* 848:79-87 (2007).

An "isolated" nucleic acid refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

"Isolated nucleic acid encoding an anti-LRP5 antibody" refers to one or more nucleic acid molecules encoding antibody heavy and light chains (or fragments thereof), including such nucleic acid molecule(s) in a single vector or separate vectors, and such nucleic acid molecule(s) present at one or more locations in a host cell.

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

A "naked antibody" refers to an antibody that is not conjugated to a heterologous moiety (e.g., a cytotoxic moiety) or radiolabel. The naked antibody may be present in a pharmaceutical formulation.

"Native antibodies" refer to naturally occurring immunoglobulin molecules with varying structures. For example, native IgG antibodies are heterotetrameric glycoproteins of about 150,000 daltons, composed of two identical light chains and two identical heavy chains that are disulfide-bonded. From N- to C-terminus, each heavy chain has a variable region (VH), also called a variable heavy domain or a heavy chain variable domain, followed by three constant domains (CH1, CH2, and CH3). Similarly, from N- to C-terminus, each light chain has a variable region (VL), also called a variable light domain or a light chain variable domain, followed by a constant light (CL) domain. The light chain of an antibody may be assigned to one of two types, called kappa (κ) and lambda (λ), based on the amino acid sequence of its constant domain.

The term "package insert" is used to refer to instructions customarily included in commercial packages of therapeutic products, that contain information about the indications, usage, dosage, administration, combination therapy, contraindications and/or warnings concerning the use of such therapeutic products.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction X/Y where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

The term "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

The term "Low-density lipoprotein receptor-related protein 5" or "LRP5," as used herein, refers to any native LRP5 from any vertebrate source, including mammals such as primates (e.g. humans) and rodents (e.g., mice and rats), unless otherwise indicated. The term encompasses "full-length," unprocessed LRP5 as well as any form of LRP5 that results from processing in the cell. The term also encompasses naturally occurring variants of LRP5, e.g., splice variants or allelic variants. The amino acid sequence of an exemplary human LRP5 is as follows:

(SEQ ID NO: 42)
MEAAPPGPPWPLLLLLLLLLALCGCPAPAAASPLLLFANRRDVRLVDAGG

VKLESTIVVSGLEDAAAVDFQFSKGAVYWTDVSEEAIKQTYLNQTGAAVQ

NVVISGLVSPDGLACDWVGKKLYWTDSETNRIEVANLNGTSRKVLFWQDL

DQPRAIALDPAHGYMYWTDWGETPRIERAGMDGSTRKIIVDSDIYWPNGL

TIDLEEQKLYWADAKLSFIHRANLDGSFRQKVVEGSLTHPFALTLSGDTL

YWTDWQTRSIHACNKRTGGKRKEILSALYSPMDIQVLSQERQPFFHTRCE

EDNGGCSHLCLLSPSEPFYTCACPTGVQLQDNGRTCKAGAEEVLLLARRT

DLRRISLDTPDFTDIVLQVDDIRHAIAIDYDPLEGYVYWTDDEVRAIRRA

YLDGSGAQTLVNTEINDPDGIAVDWVARNLYWTDTGTDRIEVTRLNGTSR

KILVSEDLDEPRAIALHPVMGLMYWTDWGENPKIECANLDGQERRVLVNA

SLGWPNGLALDLQEGKLYWGDAKTDKIEVINVDGTKRRTLLEDKLPHIFG

FTLLGDFIYWTDWQRRSIERVHKVKASRDVIIDQLPDLMGLKAVNVAKVV

GTNPCADRNGGCSHLCFFTPHATRCGCPIGLELLSDMKTCIVPEAFLVFT

SRAAIHRISLETNNNDVAIPLTGVKEASALDFDVSNNHIYWTDVSLKTIS

RAFMNGSSVEHVVEFGLDYPEGMAVDWMGKNLYWADTGTNRIEVARLDGQ

FRQVLVWRDLDNPRSLALDPTKGYIYWTEWGGKPRIVRAFMDGTNCMTLV

DKVGRANDLTIDYADQRLYWTDLDTNMIESSNMLGQERVVIADDLPHPFG

LTQYSDYIYWTDWNLHSIERADKTSGRNRTLIQGHLDFVMDILVFHSSRQ

DGLNDCMHNNGQCGQLCLAIPGGHRCGCASHYTLDPSSRNCSPPTTFLLF

SQKSAISRMIPDDQHSPDLILPLHGLRNVKAIDYDPLDKFIYWVDGRQNI

KRAKDDGTQPFVLTSLSQGQNPDRQPHDLSIDIYSRTLFWTCEATNTINV

```
-continued
HRLSGEAMGVVLRGDRDKPRAIVVNAERGYLYFTNMQDRAAKIERAALDG

TEREVLFTTGLIRPVALVVDNTLGKLFWVDADLKRIESCDLSGANRLTLE

DANIVQPLGLTILGKHLYWIDRQQQMIERVEKTTGDKRTRIQGRVAHLTG

IHAVEEVSLEEFSAHPCARDNGGCSHICIAKGDGTPRCSCPVHLVLLQNL

LTCGEPPTCSPDQFACATGEIDCIPGAWRCDGFPECDDQSDEEGCPVCSA

AQFPCARGQCVDLRLRCDGEADCQDRSDEADCDAICLPNQFRCASGQCVL

IKQQCDSFPDCIDGSDELMCEITKPPSDDSPAHSSAIGPVIGIILSLFVM

GGVYFVCQRVVCQRYAGANGPFPHEYVSGTPHVPLNFIAPGGSQHGPFTG

IACGKSMMSSVSLMGGRGGVPLYDRNHVTGASSSSSSSTKATLYPPILNP

PPSPATDPSLYNMDMFYSSNIPATARPYRPYIIRGMAPPTTPCSTDVCDS

DYSASRWKASKYYLDLNSDSDPYPPPPTPHSQYLSAEDSCPPSPATERSY

FHLFPPPPSPCTDSS.
```

As used herein, "treatment" (and grammatical variations thereof such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, antibodies of the invention are used to delay development of a disease or to slow the progression of a disease.

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs). (See, e.g., Kindt et al. *Kuby Immunology*, 6<sup>th</sup> ed., W.H. Freeman and Co., page 91 (2007).) A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See, e.g., Portolano et al., *J. Immunol.* 150:880-887 (1993); Clarkson et al., *Nature* 352:624-628 (1991).

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

II. Compositions and Methods

In one aspect, the invention is based, in part, on the discovery of antibodies that potentiate Norrin and/or Norrin/Frizzled4 signalling. In certain embodiments, antibodies that bind to LRP5 are provided. Antibodies of the invention are useful, e.g., for the diagnosis or treatment of retinopathies including proliferative diabetic retinopathy, CNV, AMD, diabetic and other ischemia-related retinopathies, DME, pathological myopia, von Hippel-Lindau disease, histoplasmosis of the eye, CRVO, BRVO, corneal neovascularization, retinal neovascularization, ROP, FEVR, Coats' disease, Norrie Disease, OPPG (Osteoporosis-Pseudoglioma Syndrome), subconjunctival hemorrhage, and hypertensive retinopathy.

A. Exemplary Anti-LRP5 Antibodies

In one aspect, the invention provides isolated antibodies that bind to LRP5. In certain embodiments, an anti-LRP5 antibody potentiates Norrin activity and/or Norrin/Fzd4 signaling.

In one aspect, the invention provides an anti-PRO antibody comprising at least one, two, three, four, five, or six HVRs selected from (a) HVR-H1 comprising the amino acid sequence of SEQ ID NO: 28; (b) HVR-H2 comprising the amino acid sequence of SEQ ID NO:26 or 27; (c) HVR-H3 comprising the amino acid sequence of SEQ ID NO: 23 or 24; (d) HVR-L1 comprising the amino acid sequence of SEQ ID NO: 29 or 30; (e) HVR-L2 comprising the amino acid sequence of SEQ ID NO: 31 or 32; and (f) HVR-L3 comprising the amino acid sequence of SEQ ID NO: 33.

In one aspect, the invention provides an antibody comprising at least one, at least two, or all three VH HVR sequences selected from (a) HVR-H1 comprising the amino acid sequence of SEQ ID NO: 28; (b) HVR-H2 comprising the amino acid sequence of SEQ ID NO: 26 or 27; and (c) HVR-H3 comprising the amino acid sequence of SEQ ID NO: 23 or 24. In one embodiment, the antibody comprises HVR-H3 comprising the amino acid sequence of SEQ ID NO: 23 or 24. In another embodiment, the antibody comprises HVR-H3 comprising the amino acid sequence of SEQ ID NO: 23 or 24 and HVR-L3 comprising the amino acid sequence of SEQ ID NO: 33. In a further embodiment, the antibody comprises HVR-H3 comprising the amino acid sequence of SEQ ID NO: 23 or 24, HVR-L3 comprising the amino acid sequence of SEQ ID NO: 33, and HVR-H2 comprising the amino acid sequence of SEQ ID NO: 26 or 27. In a further embodiment, the antibody comprises (a) HVR-H1 comprising the amino acid sequence of SEQ ID NO: 28; (b) HVR-H2 comprising the amino acid sequence of SEQ ID NO: 26 or 27; and (c) HVR-H3 comprising the amino acid sequence of SEQ ID NO: 23 or 24.

In another aspect, the invention provides an antibody comprising at least one, at least two, or all three VL HVR sequences selected from (a) HVR-L1 comprising the amino acid sequence of SEQ ID NO: 29 or 30; (b) HVR-L2 comprising the amino acid sequence of SEQ ID NO: 31 or 32; and (c) HVR-L3 comprising the amino acid sequence of SEQ ID NO: 33. In one embodiment, the antibody comprises (a) HVR-L1 comprising the amino acid sequence of SEQ ID NO: 29 or 30; (b) HVR-L2 comprising the amino acid sequence of SEQ ID NO: 31 or 32; and (c) HVR-L3 comprising the amino acid sequence of SEQ ID NO: 33.

In another aspect, an antibody of the invention comprises (a) a VH domain comprising at least one, at least two, or all three VH HVR sequences selected from (i) HVR-H1 comprising the amino acid sequence of SEQ ID NO: 28, (ii) HVR-H2 comprising the amino acid sequence of SEQ ID NO: 26 or 27, and (iii) HVR-H3 comprising an amino acid sequence selected from SEQ ID NO: 23 or 24; and (b) a VL domain comprising at least one, at least two, or all three VL HVR sequences selected from (i) HVR-L1 comprising the amino acid sequence of SEQ ID NO: 29 or 30, (ii) HVR-L2 comprising the amino acid sequence of SEQ ID NO: 31 or 32, and (c) HVR-L3 comprising the amino acid sequence of SEQ ID NO: 33.

In another aspect, the invention provides an antibody comprising (a) HVR-H1 comprising the amino acid sequence of SEQ ID NO: 28; (b) HVR-H2 comprising the amino acid sequence of SEQ ID NO: 26 or 27; (c) HVR-H3 comprising the amino acid sequence of SEQ ID NO: 23 or 24; (d) HVR-L1 comprising the amino acid sequence of SEQ ID NO: 29 or 30; (e) HVR-L2 comprising the amino acid sequence of SEQ ID NO: 31 or 32; and (0 HVR-L3 comprising an amino acid sequence selected from SEQ ID NO: 33.

In any of the above embodiments, an anti-LRP5 antibody may be humanized. In one embodiment, an anti-LRP5 antibody comprises HVRs as in any of the above embodiments, and further comprises an acceptor human framework, e.g. a human immunoglobulin framework or a human consensus framework. In another embodiment, an anti-LRP5 antibody comprises HVRs as in any of the above embodiments, and further comprises a VH or VL comprising an FR sequence, wherein the FR sequences are as follows. For the heavy chain, FR1 comprises the sequence EVQLVES-GGGLVQPGGSLRLSCAAS (SEQ ID NO: 34), FR2 comprises the sequence WVRQAPGKGLEWV (SEQ ID NO: 35), FR3 comprises the sequence RFTISRDNSKNT-LYLQMNSLRAEDTAVYYCAR (SEQ ID NO: 36), FR4 comprises the sequence WGQ (SEQ ID NO: 37). For the light chain, FR1 comprises the sequence DIQMTQSPSSLSASVGDRVTITC (SEQ ID NO: 38), FR2 comprises the sequence WYQQKPGKAPKLLIY (SEQ ID NO: 39), FR3 comprises the sequence GVPSRFSGSGS-GTDFTLTISSLQPEDFATYYC (SEQ ID NO: 40), FR4 comprises the sequence FGQGTKVEIKR (SEQ ID NO: 41).

In another aspect, an anti-LRP5 antibody comprises a heavy chain variable domain (VH) sequence having at least 90%, 91%, 92%, 93%, 94%, 95%, 96%, 97%, 98%, 99%, or 100% sequence identity to the amino acid sequence of any one of SEQ ID NOs: 1-11. In certain embodiments, a VH sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-LRP5 antibody comprising that sequence retains the ability to bind to LRP5. In certain embodiments, a total of 1 to 10 amino acids have been substituted, inserted and/or deleted in any one of SEQ ID NOs: 1-11. In certain embodiments, substitutions, insertions, or deletions occur in regions outside the HVRs (i.e., in the FRs). Optionally, the anti-LRP5 antibody comprises the VH sequence in any one of SEQ ID NOs: 1-11, including post-translational modifications of that sequence. In a particular embodiment, the VH comprises one, two or three HVRs selected from: (a) HVR-H1 comprising the amino acid sequence of SEQ ID NO: 28, (b) HVR-H2 comprising the amino acid sequence of SEQ ID NO: 26 or 27, and (c) HVR-H3 comprising the amino acid sequence of SEQ ID NO: 23 or 24.

In another aspect, an anti-LRP5 antibody is provided, wherein the antibody comprises a light chain variable domain (VL) having at least 90%, 91%, 92%, 93%, 94%, 95%, 96%, 97%, 98%, 99%, or 100% sequence identity to the amino acid sequence of SEQ ID NO: 12-22. In certain embodiments, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-PRO antibody comprising that sequence retains the ability to bind to PRO. In certain embodiments, a total of 1 to 10 amino acids have been substituted, inserted and/or deleted in SEQ ID NO: 12-22. In certain embodiments, the substitutions, insertions, or deletions occur in regions outside the HVRs (i.e., in the FRs). Optionally, the anti-LRP5 antibody comprises the VL sequence in SEQ ID NO: 12-22, including post-translational modifications of that sequence. In a particular embodiment, the VL comprises one, two or three HVRs selected from (a) HVR-L1 comprising the amino acid sequence of SEQ ID NO: 29 or 30; (b) HVR-L2 comprising the amino acid sequence of SEQ ID NO: 31 or 32; and (c) HVR-L3 comprising the amino acid sequence of SEQ ID NO: 33.

In another aspect, an anti-LRP5 antibody is provided, wherein the antibody comprises a VH as in any of the embodiments provided above, and a VL as in any of the embodiments provided above. In one embodiment, the antibody comprises the VH and VL sequences in any one of SEQ ID NOs: 1-11 and SEQ ID NOs: 12-22, respectively, including post-translational modifications of those sequences. In some embodiments, the antibody comprises VH and VL sequences as follows: SEQ ID NO: 1 and SEQ ID NO: 12, SEQ ID NO: 2 and SEQ ID NO: 13, SEQ ID NO: 3 and SEQ ID NO: 14, SEQ ID NO: 4 and SEQ ID NO: 15, SEQ ID NO: 5 and SEQ ID NO: 16, SEQ ID NO: 6 and SEQ ID NO: 17, SEQ ID NO: 7 and SEQ ID NO: 18, SEQ ID NO: 8 and SEQ ID NO: 19, SEQ ID NO: 9 and SEQ ID NO: 20, SEQ ID NO: 10 and SEQ ID NO: 21, or SEQ ID NO: 11 and SEQ ID NO: 22.

In a further aspect, the invention provides an antibody that binds to the same epitope as an anti-LRP5 antibody provided herein. For example, in certain embodiments, an antibody is provided that binds to the same epitope as an anti-LRP5 antibody comprising a VH sequence of SEQ ID NO: 1 and a VL sequence of SEQ ID NO: 12 or comprising a VH sequence of SEQ ID NO: 5 and a VL sequence of SEQ ID NO: 16.

In a further aspect of the invention, an anti-LRP5 antibody according to any of the above embodiments is a monoclonal antibody, including a chimeric, humanized or human antibody. In one embodiment, an anti-LRP5 antibody is an antibody fragment, e.g., a Fv, Fab, Fab', scFv, diabody, or F(ab')$_2$ fragment. In another embodiment, the antibody is a full length antibody, e.g., an intact IgG1 antibody or other antibody class or isotype as defined herein.

In a further aspect, an anti-LRP5 antibody according to any of the above embodiments may incorporate any of the features, singly or in combination, as described in Sections 1-7 below:

1. Antibody Affinity

In certain embodiments, an antibody provided herein has a dissociation constant (Kd) of ≤1 µM, ≤100 nM, ≤10 nM, ≤1 nM, ≤0.1 nM, ≤0.01 nM, or ≤0.001 nM (e.g. $10^{-8}$ M or less, e.g. from $10^{-8}$ M to $10^{-13}$ M, e.g., from $10^{-9}$ M to $10^{-13}$ M).

In one embodiment, Kd is measured by a radiolabeled antigen binding assay (RIA) performed with the Fab version of an antibody of interest and its antigen as described by the following assay. Solution binding affinity of Fabs for antigen is measured by equilibrating Fab with a minimal concentration of ($^{125}$I)-labeled antigen in the presence of a titration series of unlabeled antigen, then capturing bound antigen with an anti-Fab antibody-coated plate (see, e.g., Chen et al., *J. Mol. Biol.* 293:865-881(1999)). To establish conditions for the assay, MICROTITER® multi-well plates (Thermo Scientific) are coated overnight with 5 µg/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23° C.). In a non-adsorbent plate (Nunc #269620), 100 pM or 26 pM [$^{125}$I]-antigen are mixed with serial dilutions of a Fab of interest (e.g., consistent with assessment of the anti-VEGF antibody, Fab-12, in Presta et al., *Cancer Res.* 57:4593-4599 (1997)). The Fab of interest is then incubated overnight; however, the incubation may continue for a longer period (e.g., about 65 hours) to ensure that equilibrium is reached. Thereafter, the mixtures are transferred to the capture plate for incubation at room temperature (e.g., for one hour). The solution is then removed and the plate washed eight times with 0.1% polysorbate 20 (TWEEN-20®) in PBS. When the plates have dried, 150 μl/well of scintillant (MICROSCINT-20™; Packard) is added, and the plates are counted on a TOP-COUNT™ gamma counter (Packard) for ten minutes. Concentrations of each Fab that give less than or equal to 20% of maximal binding are chosen for use in competitive binding assays.

According to another embodiment, Kd is measured using surface plasmon resonance assays using a BIACORE®-2000 or a BIACORE®-3000 (BIAcore, Inc., Piscataway, N.J.) at 25° C. with immobilized antigen CM5 chips at ~10 response units (RU). Briefly, carboxymethylated dextran biosensor chips (CM5, BIACORE, Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, to 5 μg/ml (~0.2 μM) before injection at a flow rate of 5 μl/minute to achieve approximately 10 response units (RU) of coupled protein. Following the injection of antigen, 1 M ethanolamine is injected to block unreacted groups. For kinetics measurements, two-fold serial dilutions of Fab (0.78 nM to 500 nM) are injected in PBS with 0.05% polysorbate 20 (TWEEN-20™) surfactant (PBST) at 25° C. at a flow rate of approximately 25 μl/min. Association rates ($k_{on}$) and dissociation rates ($k_{off}$) are calculated using a simple one-to-one Langmuir binding model (BIACORE® Evaluation Software version 3.2) by simultaneously fitting the association and dissociation sensorgrams. The equilibrium dissociation constant (Kd) is calculated as the ratio $k_{off}/k_{on}$. See, e.g., Chen et al., *J. Mol. Biol.* 293:865-881 (1999). If the on-rate exceeds $10^6$ $M^{-1}$ $s^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophometer (Aviv Instruments) or a 8000-series SLM-AMINCO™ spectrophotometer (ThermoSpectronic) with a stirred cuvette.

2. Antibody Fragments

In certain embodiments, an antibody provided herein is an antibody fragment. Antibody fragments include, but are not limited to, Fab, Fab', Fab'-SH, F(ab')$_2$, Fv, and scFv fragments, and other fragments described below. For a review of certain antibody fragments, see Hudson et al. *Nat. Med.* 9:129-134 (2003). For a review of scFv fragments, see, e.g., Plückthün, in *The Pharmacology of Monoclonal Antibodies*, vol. 113, Rosenburg and Moore eds., (Springer-Verlag, New York), pp. 269-315 (1994); see also WO 93/16185; and U.S. Pat. Nos. 5,571,894 and 5,587,458. For discussion of Fab and F(ab')$_2$ fragments comprising salvage receptor binding epitope residues and having increased in vivo half-life, see U.S. Pat. No. 5,869,046.

Diabodies are antibody fragments with two antigen-binding sites that may be bivalent or bispecific. See, for example, EP 404,097; WO 1993/01161; Hudson et al., *Nat. Med.* 9:129-134 (2003); and Hollinger et al., *Proc. Natl. Acad. Sci. USA* 90: 6444-6448 (1993). Triabodies and tetrabodies are also described in Hudson et al., *Nat. Med.* 9:129-134 (2003).

Single-domain antibodies are antibody fragments comprising all or a portion of the heavy chain variable domain or all or a portion of the light chain variable domain of an antibody. In certain embodiments, a single-domain antibody is a human single-domain antibody (Domantis, Inc., Waltham, Mass.; see, e.g., U.S. Pat. No. 6,248,516 B1).

Antibody fragments can be made by various techniques, including but not limited to proteolytic digestion of an intact antibody as well as production by recombinant host cells (e.g. *E. coli* or phage), as described herein.

3. Chimeric and Humanized Antibodies

In certain embodiments, an antibody provided herein is a chimeric antibody. Certain chimeric antibodies are described, e.g., in U.S. Pat. No. 4,816,567; and Morrison et al., *Proc. Natl. Acad. Sci. USA*, 81:6851-6855 (1984)). In one example, a chimeric antibody comprises a non-human variable region (e.g., a variable region derived from a mouse, rat, hamster, rabbit, or non-human primate, such as a monkey) and a human constant region. In a further example, a chimeric antibody is a "class switched" antibody in which the class or subclass has been changed from that of the parent antibody. Chimeric antibodies include antigen-binding fragments thereof.

In certain embodiments, a chimeric antibody is a humanized antibody. Typically, a non-human antibody is humanized to reduce immunogenicity to humans, while retaining the specificity and affinity of the parental non-human antibody. Generally, a humanized antibody comprises one or more variable domains in which HVRs, e.g., CDRs, (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived), e.g., to restore or improve antibody specificity or affinity.

Humanized antibodies and methods of making them are reviewed, e.g., in Almagro and Fransson, *Front. Biosci.* 13:1619-1633 (2008), and are further described, e.g., in Riechmann et al., *Nature* 332:323-329 (1988); Queen et al., *Proc. Nat'l Acad. Sci. USA* 86:10029-10033 (1989); U.S. Pat. Nos. 5,821,337, 7,527,791, 6,982,321, and 7,087,409; Kashmiri et al., *Methods* 36:25-34 (2005) (describing SDR (a-CDR) grafting); Padlan, *Mol. Immunol.* 28:489-498 (1991) (describing "resurfacing"); Dall'Acqua et al., *Methods* 36:43-60 (2005) (describing "FR shuffling"); and Osbourn et al., *Methods* 36:61-68 (2005) and Klimka et al., *Br. J. Cancer,* 83:252-260 (2000) (describing the "guided selection" approach to FR shuffling).

Human framework regions that may be used for humanization include but are not limited to: framework regions selected using the "best-fit" method (see, e.g., Sims et al. *J. Immunol.* 151:2296 (1993)); framework regions derived from the consensus sequence of human antibodies of a particular subgroup of light or heavy chain variable regions (see, e.g., Carter et al. *Proc. Natl. Acad. Sci. USA,* 89:4285

(1992); and Presta et al. *J. Immunol.,* 151:2623 (1993)); human mature (somatically mutated) framework regions or human germline framework regions (see, e.g., Almagro and Fransson, *Front. Biosci.* 13:1619-1633 (2008)); and framework regions derived from screening FR libraries (see, e.g., Baca et al., *J. Biol. Chem.* 272:10678-10684 (1997) and Rosok et al., *J. Biol. Chem.* 271:22611-22618 (1996)).

4. Human Antibodies

In certain embodiments, an antibody provided herein is a human antibody. Human antibodies can be produced using various techniques known in the art. Human antibodies are described generally in van Dijk and van de Winkel, *Curr. Opin. Pharmacol.* 5: 368-74 (2001) and Lonberg, *Curr. Opin. Immunol.* 20:450-459 (2008).

Human antibodies may be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. For review of methods for obtaining human antibodies from transgenic animals, see Lonberg, *Nat. Biotech.* 23:1117-1125 (2005). See also, e.g., U.S. Pat. Nos. 6,075,181 and 6,150,584 describing XENO-MOUSE™ technology; U.S. Pat. No. 5,770,429 describing HuMab® technology; U.S. Pat. No. 7,041,870 describing K-M MOUSE® technology, and U.S. Patent Application Publication No. US 2007/0061900, describing VELOCI-MOUSE® technology). Human variable regions from intact antibodies generated by such animals may be further modified, e.g., by combining with a different human constant region.

Human antibodies can also be made by hybridoma-based methods. Human myeloma and mouse-human heteromyeloma cell lines for the production of human monoclonal antibodies have been described. (See, e.g., Kozbor *J. Immunol.,* 133: 3001 (1984); Brodeur et al., *Monoclonal Antibody Production Techniques and Applications,* pp. 51-63 (Marcel Dekker, Inc., New York, 1987); and Boerner et al., *J. Immunol.,* 147: 86 (1991).) Human antibodies generated via human B-cell hybridoma technology are also described in Li et al., *Proc. Natl. Acad. Sci. USA,* 103:3557-3562 (2006). Additional methods include those described, for example, in U.S. Pat. No. 7,189,826 (describing production of monoclonal human IgM antibodies from hybridoma cell lines) and Ni, *Xiandai Mianyixue,* 26(4):265-268 (2006) (describing human-human hybridomas). Human hybridoma technology (Trioma technology) is also described in Vollmers and Brandlein, *Histology and Histopathology,* 20(3):927-937 (2005) and Vollmers and Brandlein, *Methods and Findings in Experimental and Clinical Pharmacology,* 27(3):185-91 (2005).

Human antibodies may also be generated by isolating Fv clone variable domain sequences selected from human-derived phage display libraries. Such variable domain sequences may then be combined with a desired human constant domain. Techniques for selecting human antibodies from antibody libraries are described below.

5. Library-Derived Antibodies

Antibodies of the invention may be isolated by screening combinatorial libraries for antibodies with the desired activity or activities. For example, a variety of methods are known in the art for generating phage display libraries and screening such libraries for antibodies possessing the desired binding characteristics. Such methods are reviewed, e.g., in Hoogenboom et al. in *Methods in Molecular Biology* 178: 1-37 (O'Brien et al., ed., Human Press, Totowa, N.J., 2001) and further described, e.g., in the McCafferty et al., *Nature* 348:552-554; Clackson et al., *Nature* 352: 624-628 (1991); Marks et al., *J. Mol. Biol.* 222: 581-597 (1992); Marks and Bradbury, in *Methods in Molecular Biology* 248:161-175 (Lo, ed., Human Press, Totowa, N.J., 2003); Sidhu et al., *J. Mol. Biol.* 338(2): 299-310 (2004); Lee et al., *J. Mol. Biol.* 340(5): 1073-1093 (2004); Fellouse, *Proc. Natl. Acad. Sci. USA* 101(34): 12467-12472 (2004); and Lee et al., *J. Immunol. Methods* 284(1-2): 119-132(2004).

In certain phage display methods, repertoires of VH and VL genes are separately cloned by polymerase chain reaction (PCR) and recombined randomly in phage libraries, which can then be screened for antigen-binding phage as described in Winter et al., *Ann. Rev. Immunol.,* 12: 433-455 (1994). Phage typically display antibody fragments, either as single-chain Fv (scFv) fragments or as Fab fragments. Libraries from immunized sources provide high-affinity antibodies to the immunogen without the requirement of constructing hybridomas. Alternatively, the naive repertoire can be cloned (e.g., from human) to provide a single source of antibodies to a wide range of non-self and also self antigens without any immunization as described by Griffiths et al., *EMBO J,* 12: 725-734 (1993). Finally, naive libraries can also be made synthetically by cloning unrearranged V-gene segments from stem cells, and using PCR primers containing random sequence to encode the highly variable CDR3 regions and to accomplish rearrangement in vitro, as described by Hoogenboom and Winter, *J. Mol. Biol.,* 227: 381-388 (1992). Patent publications describing human antibody phage libraries include, for example: U.S. Pat. No. 5,750,373, and US Patent Publication Nos. 2005/0079574, 2005/0119455, 2005/0266000, 2007/0117126, 2007/0160598, 2007/0237764, 2007/0292936, and 2009/0002360.

Antibodies or antibody fragments isolated from human antibody libraries are considered human antibodies or human antibody fragments herein.

6. Multispecific Antibodies

In certain embodiments, an antibody provided herein is a multispecific antibody, e.g. a bispecific antibody. Multispecific antibodies are monoclonal antibodies that have binding specificities for at least two different sites. In certain embodiments, one of the binding specificities is for LRP5 and the other is for any other antigen. In certain embodiments, the other binding specificity if for vascular endothelial growth factor (VEGF). In certain embodiments, bispecific antibodies may bind to two different epitopes of LRP5. Bispecific antibodies may also be used to localize cytotoxic agents to cells which express LRP5. Bispecific antibodies can be prepared as full length antibodies or antibody fragments.

Techniques for making multispecific antibodies include, but are not limited to, recombinant co-expression of two immunoglobulin heavy chain-light chain pairs having different specificities (see Milstein and Cuello, *Nature* 305: 537 (1983)), WO 93/08829, and Traunecker et al., *EMBO J.* 10: 3655 (1991)), and "knob-in-hole" engineering (see, e.g., U.S. Pat. No. 5,731,168). Multi-specific antibodies may also be made by engineering electrostatic steering effects for making antibody Fc-heterodimeric molecules (WO 2009/089004A1); cross-linking two or more antibodies or fragments (see, e.g., U.S. Pat. No. 4,676,980, and Brennan et al., *Science,* 229: 81 (1985)); using leucine zippers to produce bi-specific antibodies (see, e.g., Kostelny et al., *J. Immunol.,*

148(5):1547-1553 (1992)); using "diabody" technology for making bispecific antibody fragments (see, e.g., Hollinger et al., *Proc. Natl. Acad. Sci. USA,* 90:6444-6448 (1993)); and using single-chain Fv (sFv) dimers (see, e.g. Gruber et al., *J. Immunol.,* 152:5368 (1994)); and preparing trispecific antibodies as described, e.g., in Tutt et al. *J. Immunol.* 147: 60 (1991).

Engineered antibodies with three or more functional antigen binding sites, including "Octopus antibodies," are also included herein (see, e.g. US 2006/0025576A1).

The antibody or fragment herein also includes a "Dual Acting FAb" or "DAF" comprising an antigen binding site that binds to LRP5 as well as another, different antigen (see, US 2008/0069820, for example).

7. Antibody Variants

In certain embodiments, amino acid sequence variants of the antibodies provided herein are contemplated. For example, it may be desirable to improve the binding affinity and/or other biological properties of the antibody. Amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen-binding.

a) Substitution, Insertion, and Deletion Variants

In certain embodiments, antibody variants having one or more amino acid substitutions are provided. Sites of interest for substitutional mutagenesis include the HVRs and FRs. Conservative substitutions are shown in Table 1 under the heading of "conservative substitutions." More substantial changes are provided in Table 1 under the heading of "exemplary substitutions," and as further described below in reference to amino acid side chain classes. Amino acid substitutions may be introduced into an antibody of interest and the products screened for a desired activity, e.g., retained/improved antigen binding, decreased immunogenicity, or improved ADCC or CDC.

TABLE 1

| Original Residue | Exemplary Substitutions | Preferred Substitutions |
| --- | --- | --- |
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:
(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class.

One type of substitutional variant involves substituting one or more hypervariable region residues of a parent antibody (e.g. a humanized or human antibody). Generally, the resulting variant(s) selected for further study will have modifications (e.g., improvements) in certain biological properties (e.g., increased affinity, reduced immunogenicity) relative to the parent antibody and/or will have substantially retained certain biological properties of the parent antibody. An exemplary substitutional variant is an affinity matured antibody, which may be conveniently generated, e.g., using phage display-based affinity maturation techniques such as those described herein. Briefly, one or more HVR residues are mutated and the variant antibodies displayed on phage and screened for a particular biological activity (e.g. binding affinity).

Alterations (e.g., substitutions) may be made in HVRs, e.g., to improve antibody affinity. Such alterations may be made in HVR "hotspots," i.e., residues encoded by codons that undergo mutation at high frequency during the somatic maturation process (see, e.g., Chowdhury, *Methods Mol. Biol.* 207:179-196 (2008)), and/or SDRs (a-CDRs), with the resulting variant VH or VL being tested for binding affinity. Affinity maturation by constructing and reselecting from secondary libraries has been described, e.g., in Hoogenboom et al. in *Methods in Molecular Biology* 178:1-37 (O'Brien et al., ed., Human Press, Totowa, N.J., (2001).) In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves HVR-directed approaches, in which several HVR residues (e.g., 4-6 residues at a time) are randomized. HVR residues involved in antigen binding may be specifically identified, e.g., using alanine scanning mutagenesis or modeling. CDR-H3 and CDR-L3 in particular are often targeted.

In certain embodiments, substitutions, insertions, or deletions may occur within one or more HVRs so long as such alterations do not substantially reduce the ability of the antibody to bind antigen. For example, conservative alterations (e.g., conservative substitutions as provided herein) that do not substantially reduce binding affinity may be made in HVRs. Such alterations may be outside of HVR "hotspots" or SDRs. In certain embodiments of the variant VH and VL sequences provided above, each HVR either is unaltered, or contains no more than one, two or three amino acid substitutions.

A useful method for identification of residues or regions of an antibody that may be targeted for mutagenesis is called "alanine scanning mutagenesis" as described by Cunningham and Wells (1989) *Science,* 244:1081-1085. In this method, a residue or group of target residues (e.g., charged residues such as arg, asp, his, lys, and glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g. for ADEPT) or a polypeptide which increases the serum half-life of the antibody.

b) Glycosylation Variants

In certain embodiments, an antibody provided herein is altered to increase or decrease the extent to which the antibody is glycosylated. Addition or deletion of glycosylation sites to an antibody may be conveniently accomplished by altering the amino acid sequence such that one or more glycosylation sites is created or removed.

Where the antibody comprises an Fc region, the carbohydrate attached thereto may be altered. Native antibodies produced by mammalian cells typically comprise a branched, biantennary oligosaccharide that is generally attached by an N-linkage to Asn297 of the CH2 domain of the Fc region. See, e.g., Wright et al. *TIBTECH* 15:26-32 (1997). The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an antibody of the invention may be made in order to create antibody variants with certain improved properties.

In one embodiment, antibody variants are provided having a carbohydrate structure that lacks fucose attached (directly or indirectly) to an Fc region. For example, the amount of fucose in such antibody may be from 1% to 80%, from 1% to 65%, from 5% to 65% or from 20% to 40%. The amount of fucose is determined by calculating the average amount of fucose within the sugar chain at Asn297, relative to the sum of all glycostructures attached to Asn 297 (e. g. complex, hybrid and high mannose structures) as measured by MALDI-TOF mass spectrometry, as described in WO 2008/077546, for example. Asn297 refers to the asparagine residue located at about position 297 in the Fc region (Eu numbering of Fc region residues); however, Asn297 may also be located about ±3 amino acids upstream or downstream of position 297, i.e., between positions 294 and 300, due to minor sequence variations in antibodies. Such fucosylation variants may have improved ADCC function. See, e.g., US Patent Publication Nos. US 2003/0157108 (Presta, L.); US 2004/0093621 (Kyowa Hakko Kogyo Co., Ltd). Examples of publications related to "defucosylated" or "fucose-deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; WO2002/031140; Okazaki et al. *J. Mol. Biol.* 336:1239-1249 (2004); Yamane-Ohnuki et al. *Biotech. Bioeng.* 87: 614 (2004). Examples of cell lines capable of producing defucosylated antibodies include Lec13 CHO cells deficient in protein fucosylation (Ripka et al. *Arch. Biochem. Biophys.* 249:533-545 (1986); US Pat Appl No US 2003/0157108 A1, Presta, L; and WO 2004/056312 A1, Adams et al., especially at Example 11), and knockout cell lines, such as alpha-1,6-fucosyltransferase gene, FUT8, knockout CHO cells (see, e.g., Yamane-Ohnuki et al. *Biotech. Bioeng.* 87: 614 (2004); Kanda, Y. et al., *Biotechnol. Bioeng.*, 94(4):680-688 (2006); and WO2003/085107).

Antibodies variants are further provided with bisected oligosaccharides, e.g., in which a biantennary oligosaccharide attached to the Fc region of the antibody is bisected by GlcNAc. Such antibody variants may have reduced fucosylation and/or improved ADCC function. Examples of such antibody variants are described, e.g., in WO 2003/011878 (Jean-Mairet et al.); U.S. Pat. No. 6,602,684 (Umana et al.); and US 2005/0123546 (Umana et al.). Antibody variants with at least one galactose residue in the oligosaccharide attached to the Fc region are also provided. Such antibody variants may have improved CDC function. Such antibody variants are described, e.g., in WO 1997/30087 (Patel et al.); WO 1998/58964 (Raju, S.); and WO 1999/22764 (Raju, S.).

c) Fc Region Variants

In certain embodiments, one or more amino acid modifications may be introduced into the Fc region of an antibody provided herein, thereby generating an Fc region variant. The Fc region variant may comprise a human Fc region sequence (e.g., a human IgG1, IgG2, IgG3 or IgG4 Fc region) comprising an amino acid modification (e.g. a substitution) at one or more amino acid positions.

In certain embodiments, the invention contemplates an antibody variant that possesses some but not all effector functions, which make it a desirable candidate for applications in which the half life of the antibody in vivo is important yet certain effector functions (such as complement and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express Fc(RIII only, whereas monocytes express Fc(RI, Fc(RII and Fc(RIII. FcR expression on hematopoietic cells is summarized in Table 3 on page 464 of Ravetch and Kinet, *Annu. Rev. Immunol.* 9:457-492 (1991). Non-limiting examples of in vitro assays to assess ADCC activity of a molecule of interest is described in U.S. Pat. No. 5,500,362 (see, e.g. Hellstrom, I. et al. *Proc. Nat'l Acad. Sci. USA* 83:7059-7063 (1986)) and Hellstrom, I et al., *Proc. Nat'l Acad. Sci. USA* 82:1499-1502 (1985); U.S. Pat. No. 5,821,337 (see Bruggemann, M. et al., *J. Exp. Med.* 166:1351-1361 (1987)). Alternatively, non-radioactive assays methods may be employed (see, for example, ACTI™ non-radioactive cytotoxicity assay for flow cytometry (CellTechnology, Inc. Mountain View, Calif.; and CytoTox 96® non-radioactive cytotoxicity assay (Promega, Madison, Wis.). Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. *Proc. Nat'l Acad. Sci. USA* 95:652-656 (1998). C1q binding assays may also be carried out to confirm that the antibody is unable to bind C1q and hence lacks CDC activity. See, e.g., C1q and C3c binding ELISA in WO 2006/029879 and WO 2005/100402. To assess complement activation, a CDC assay may be performed (see, for example, Gazzano-Santoro et al., *J. Immunol. Methods* 202:163 (1996); Cragg, M. S. et al., *Blood* 101:1045-1052 (2003); and Cragg, M. S. and M. J. Glennie,

*Blood* 103:2738-2743 (2004)). FcRn binding and in vivo clearance/half life determinations can also be performed using methods known in the art (see, e.g., Petkova, S. B. et al., *Int'l. Immunol.* 18(12):1759-1769 (2006)).

Antibodies with reduced effector function include those with substitution of one or more of Fc region residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

Certain antibody variants with improved or diminished binding to FcRs are described. (See, e.g., U.S. Pat. No. 6,737,056; WO 2004/056312, and Shields et al., *J. Biol. Chem.* 9(2): 6591-6604 (2001).)

In certain embodiments, an antibody variant comprises an Fc region with one or more amino acid substitutions which improve ADCC, e.g., substitutions at positions 298, 333, and/or 334 of the Fc region (EU numbering of residues).

In some embodiments, alterations are made in the Fc region that result in altered (i.e., either improved or diminished) C1q binding and/or Complement Dependent Cytotoxicity (CDC), e.g., as described in U.S. Pat. No. 6,194,551, WO 99/51642, and Idusogie et al. *J. Immunol.* 164: 4178-4184 (2000).

Antibodies with increased half lives and improved binding to the neonatal Fc receptor (FcRn), which is responsible for the transfer of maternal IgGs to the fetus (Guyer et al., *J. Immunol.* 117:587 (1976) and Kim et al., *J. Immunol.* 24:249 (1994)), are described in US2005/0014934A1 (Hinton et al.). Those antibodies comprise an Fc region with one or more substitutions therein which improve binding of the Fc region to FcRn. Such Fc variants include those with substitutions at one or more of Fc region residues: 238, 256, 265, 272, 286, 303, 305, 307, 311, 312, 317, 340, 356, 360, 362, 376, 378, 380, 382, 413, 424 or 434, e.g., substitution of Fc region residue 434 (U.S. Pat. No. 7,371,826).

See also Duncan & Winter, *Nature* 322:738-40 (1988); U.S. Pat. No. 5,648,260; U.S. Pat. No. 5,624,821; and WO 94/29351 concerning other examples of Fc region variants.

d) Cysteine Engineered Antibody Variants

In certain embodiments, it may be desirable to create cysteine engineered antibodies, e.g., "thioMAbs," in which one or more residues of an antibody are substituted with cysteine residues. In particular embodiments, the substituted residues occur at accessible sites of the antibody. By substituting those residues with cysteine, reactive thiol groups are thereby positioned at accessible sites of the antibody and may be used to conjugate the antibody to other moieties, such as drug moieties or linker-drug moieties, to create an immunoconjugate, as described further herein. In certain embodiments, any one or more of the following residues may be substituted with cysteine: V205 (Kabat numbering) of the light chain; A118 (EU numbering) of the heavy chain; and S400 (EU numbering) of the heavy chain Fc region. Cysteine engineered antibodies may be generated as described, e.g., in U.S. Pat. No. 7,521,541.

e) Antibody Derivatives

In certain embodiments, an antibody provided herein may be further modified to contain additional nonproteinaceous moieties that are known in the art and readily available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1, 3-dioxolane, poly-1,3,6-trioxane, ethylene/maleic anhydride copolymer, polyaminoacids (either homopolymers or random copolymers), and dextran or poly(n-vinyl pyrrolidone) polyethylene glycol, propropylene glycol homopolymers, prolpropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer are attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

In another embodiment, conjugates of an antibody and nonproteinaceous moiety that may be selectively heated by exposure to radiation are provided. In one embodiment, the nonproteinaceous moiety is a carbon nanotube (Kam et al., *Proc. Natl. Acad. Sci. USA* 102: 11600-11605 (2005)). The radiation may be of any wavelength, and includes, but is not limited to, wavelengths that do not harm ordinary cells, but which heat the nonproteinaceous moiety to a temperature at which cells proximal to the antibody-nonproteinaceous moiety are killed.

B. Recombinant Methods and Compositions

Antibodies may be produced using recombinant methods and compositions, e.g., as described in U.S. Pat. No. 4,816,567. In one embodiment, isolated nucleic acid encoding an anti-LRP5 antibody described herein is provided. Such nucleic acid may encode an amino acid sequence comprising the VL and/or an amino acid sequence comprising the VH of the antibody (e.g., the light and/or heavy chains of the antibody). In a further embodiment, one or more vectors (e.g., expression vectors) comprising such nucleic acid are provided. In a further embodiment, a host cell comprising such nucleic acid is provided. In one such embodiment, a host cell comprises (e.g., has been transformed with): (1) a vector comprising a nucleic acid that encodes an amino acid sequence comprising the VL of the antibody and an amino acid sequence comprising the VH of the antibody, or (2) a first vector comprising a nucleic acid that encodes an amino acid sequence comprising the VL of the antibody and a second vector comprising a nucleic acid that encodes an amino acid sequence comprising the VH of the antibody. In one embodiment, the host cell is eukaryotic, e.g. a Chinese Hamster Ovary (CHO) cell or lymphoid cell (e.g., Y0, NS0, Sp20 cell). In one embodiment, a method of making an anti-LRP5 antibody is provided, wherein the method comprises culturing a host cell comprising a nucleic acid encoding the antibody, as provided above, under conditions suitable for expression of the antibody, and optionally recovering the antibody from the host cell (or host cell culture medium).

For recombinant production of an anti-LRP5 antibody, nucleic acid encoding an antibody, e.g., as described above, is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody).

Suitable host cells for cloning or expression of antibody-encoding vectors include prokaryotic or eukaryotic cells described herein. For example, antibodies may be produced in bacteria, in particular when glycosylation and Fc effector function are not needed. For expression of antibody fragments and polypeptides in bacteria, see, e.g., U.S. Pat. Nos. 5,648,237, 5,789,199, and 5,840,523. (See also Charlton, *Methods in Molecular Biology*, Vol. 248 (B. K. C. Lo, ed., Humana Press, Totowa, N.J., 2003), pp. 245-254, describing expression of antibody fragments in *E. coli*.) After expression, the antibody may be isolated from the bacterial cell paste in a soluble fraction and can be further purified.

In addition to prokaryotes, eukaryotic microbes such as filamentous fungi or yeast are suitable cloning or expression hosts for antibody-encoding vectors, including fungi and yeast strains whose glycosylation pathways have been "humanized," resulting in the production of an antibody with a partially or fully human glycosylation pattern. See Gerngross, *Nat. Biotech.* 22:1409-1414 (2004), and Li et al., *Nat. Biotech.* 24:210-215 (2006).

Suitable host cells for the expression of glycosylated antibody are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells.

Plant cell cultures can also be utilized as hosts. See, e.g., U.S. Pat. Nos. 5,959,177, 6,040,498, 6,420,548, 7,125,978, and 6,417,429 (describing PLANTIBODIES™ technology for producing antibodies in transgenic plants).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham et al., *J. Gen Virol.* 36:59 (1977)); baby hamster kidney cells (BHK); mouse sertoli cells (TM4 cells as described, e.g., in Mather, *Biol. Reprod.* 23:243-251 (1980)); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TRI cells, as described, e.g., in Mather et al., *Annals N.Y. Acad. Sci.* 383:44-68 (1982); MRC 5 cells; and FS4 cells. Other useful mammalian host cell lines include Chinese hamster ovary (CHO) cells, including DHFR⁻ CHO cells (Urlaub et al., *Proc. Natl. Acad. Sci. USA* 77:4216 (1980)); and myeloma cell lines such as Y0, NS0 and Sp2/0. For a review of certain mammalian host cell lines suitable for antibody production, see, e.g., Yazaki and Wu, *Methods in Molecular Biology,* Vol. 248 (B. K. C. Lo, ed., Humana Press, Totowa, N.J.), pp. 255-268 (2003).

C. Assays

Anti-LRP5 antibodies provided herein may be identified, screened for, or characterized for their physical/chemical properties and/or biological activities by various assays known in the art.

1. Binding Assays and Other Assays

In one aspect, an antibody of the invention is tested for its antigen binding activity, e.g., by known methods such as ELISA, Western blot, etc.

In another aspect, competition assays may be used to identify an antibody that competes with YW629.42 or YW629.51 for binding to LRP5. In certain embodiments, such a competing antibody binds to the same epitope (e.g., a linear or a conformational epitope) that is bound by YW629.42 or YW629.51. Detailed exemplary methods for mapping an epitope to which an antibody binds are provided in Morris (1996) "Epitope Mapping Protocols," in *Methods in Molecular Biology* vol. 66 (Humana Press, Totowa, N.J.).

In an exemplary competition assay, immobilized LRP5 is incubated in a solution comprising a first labeled antibody that binds to LRP5 (e.g., YW629.42 or YW629.51) and a second unlabeled antibody that is being tested for its ability to compete with the first antibody for binding to LRP5. The second antibody may be present in a hybridoma supernatant. As a control, immobilized LRP5 is incubated in a solution comprising the first labeled antibody but not the second unlabeled antibody. After incubation under conditions permissive for binding of the first antibody to LRP5, excess unbound antibody is removed, and the amount of label associated with immobilized LRP5 is measured. If the amount of label associated with immobilized LRP5 is substantially reduced in the test sample relative to the control sample, then that indicates that the second antibody is competing with the first antibody for binding to LRP5. See Harlow and Lane (1988) *Antibodies: A Laboratory Manual* ch. 14 (Cold Spring Harbor Laboratory, Cold Spring Harbor, N.Y.).

2. Activity Assays

In one aspect, assays are provided for identifying anti-LRP5 antibodies thereof having a biological activity. Biological activity may include, e.g., binding to LRP5, potentiation of Norrin activity, or potentiation of Norrin/Fzd4 signaling. Antibodies having such biological activity in vivo and/or in vitro are also provided.

In certain embodiments, an antibody of the invention is tested for such biological activity. In an exemplary Wnt/Norrin activation assay, LRP5 and Fzd4 protein, or relevant variants (ie. Fzd4$_{M157V}$) are transiently expressed with Topflash luciferase reporter plasmids in 293T cells. Cells expressing these proteins are exposed to Norrin or Wnt ligands and, following an incubation for 16 hours at 37° C., the level of activation is ascertained by measuring the amount of luminescence from luciferase. If the amount of luminescence is substantially increased by ligand addition in the presence of LRP5 antibody then that indicates that the antibody potentiates Fzd4/Norrin signaling. When using Fzd4$_{M157V}$, which has diminished signaling in the presence of Norrin, the increase in luminescence in the presence of LRP5 antibody is considered to rescue the defect in Fzd4 signaling.

In an additional Wnt/Norrin activation assay, cultured human retinal endothelial cells can be exposed to Norrin or Wnt ligands in the presence of LRP5 antibody or control antibody for 24-48 hours and the level of known Wnt reporter genes (ie. Axin-2 or PV-1) can be determined by quantitative RT-PCR. In the control antibody situation, following addition of Norrin and Wnt ligands, the amount of Axin-2 RNA will increase, while the amount of PV-1 RNA will decrease, relative to no ligand addition. If the presence of the LRP5 antibody, potentiation of Norrin signaling would result in a further increase in Axin-2 and conversely, decrease in PV-1. This assay can also be done in cells treated with siRNA to decrease the expression of Tspan12. In cells with diminished expression of Tspan12 there is no change in Axin-2 in the presence of Norrin. If the LRP5 antibody, but not control antibody, is able to cause an increase in Axin-2 in the absence of Tspan12 expression, then this antibody is considered to rescue the defect in Fzd4/Norrin signaling resulting from loss of Tspan12.

D. Immunoconjugates

The invention also provides immunoconjugates comprising an anti-LRP5 antibody herein conjugated to one or more cytotoxic agents, such as chemotherapeutic agents or drugs, growth inhibitory agents, toxins (e.g., protein toxins, enzymatically active toxins of bacterial, fungal, plant, or animal origin, or fragments thereof), or radioactive isotopes.

In one embodiment, an immunoconjugate is an antibody-drug conjugate (ADC) in which an antibody is conjugated to one or more drugs, including but not limited to a maytansinoid (see U.S. Pat. Nos. 5,208,020, 5,416,064 and European Patent EP 0 425 235 B1); an auristatin such as monomethylauristatin drug moieties DE and DF (MMAE and MMAF) (see U.S. Pat. Nos. 5,635,483 and 5,780,588, and 7,498,298); a dolastatin; a calicheamicin or derivative thereof (see U.S. Pat. Nos. 5,712,374, 5,714,586, 5,739,116, 5,767,285, 5,770,701, 5,770,710, 5,773,001, and 5,877,296; Hinman et al., *Cancer Res.* 53:3336-3342 (1993); and Lode et al., *Cancer Res.* 58:2925-2928 (1998)); an anthracycline such as daunomycin or doxorubicin (see Kratz et al., *Current Med. Chem.* 13:477-523 (2006); Jeffrey et al., *Bioorganic & Med. Chem. Letters* 16:358-362 (2006); Torgov et al., *Bioconj. Chem.* 16:717-721 (2005); Nagy et al., *Proc. Natl. Acad. Sci. USA* 97:829-834 (2000); Dubowchik et al., *Bioorg. & Med. Chem. Letters* 12:1529-1532 (2002); King et al., *J. Med. Chem.* 45:4336-4343 (2002); and U.S. Pat. No. 6,630,579); methotrexate; vindesine; a taxane such as docetaxel, paclitaxel, larotaxel, tesetaxel, and ortataxel; a trichothecene; and CC1065.

In another embodiment, an immunoconjugate comprises an antibody as described herein conjugated to an enzymatically active toxin or fragment thereof, including but not limited to diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, *sapaonaria officinalis* inhibitor, gelonin, mitogellin, restrictocin, phenomycin, enomycin, and the tricothecenes.

In another embodiment, an immunoconjugate comprises an antibody as described herein conjugated to a radioactive atom to form a radioconjugate. A variety of radioactive isotopes are available for the production of radioconjugates. Examples include $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu. When the radioconjugate is used for detection, it may comprise a radioactive atom for scintigraphic studies, for example tc99m or I123, or a spin label for nuclear magnetic resonance (NMR) imaging (also known as magnetic resonance imaging, mri), such as iodine-123 again, iodine-131, indium-111, fluorine-19, carbon-13, nitrogen-15, oxygen-17, gadolinium, manganese or iron.

Conjugates of an antibody and cytotoxic agent may be made using a variety of bifunctional protein coupling agents such as N-succinimidyl-3-(2-pyridyldithio) propionate (SPDP), succinimidyl-4-(N-maleimidomethyl) cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., *Science* 238:1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026. The linker may be a "cleavable linker" facilitating release of a cytotoxic drug in the cell. For example, an acid-labile linker, peptidase-sensitive linker, photolabile linker, dimethyl linker or disulfide-containing linker (Chari et al., *Cancer Res.* 52:127-131 (1992); U.S. Pat. No. 5,208,020) may be used.

The immunuoconjugates or ADCs herein expressly contemplate, but are not limited to such conjugates prepared with cross-linker reagents including, but not limited to, BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate) which are commercially available (e.g., from Pierce Biotechnology, Inc., Rockford, Ill., U.S.A).

E. Methods and Compositions for Diagnostics and Detection

In certain embodiments, any of the anti-LRP5 antibodies provided herein is useful for detecting the presence of LRP5 in a biological sample. The term "detecting" as used herein encompasses quantitative or qualitative detection. In certain embodiments, a biological sample comprises a cell or tissue, such as ocular tissue, including retinal tissue.

In one embodiment, an anti-LRP5 antibody for use in a method of diagnosis or detection is provided. In a further aspect, a method of detecting the presence of LRP5 in a biological sample is provided. In certain embodiments, the method comprises contacting the biological sample with an anti-LRP5 antibody as described herein under conditions permissive for binding of the anti-LRP5 antibody to LRP5, and detecting whether a complex is formed between the anti-LRP5 antibody and LRP5. Such method may be an in vitro or in vivo method. In one embodiment, an anti-LRP5 antibody is used to select subjects eligible for therapy with an anti-LRP5 antibody, e.g. where LRP5 is a biomarker for selection of patients.

Exemplary disorders that may be diagnosed using an antibody of the invention include retinopathies including proliferative diabetic retinopathy, CNV, AMD, diabetic and other ischemia-related retinopathies, DME, pathological myopia, von Hippel-Lindau disease, histoplasmosis of the eye, CRVO, BRVO, corneal neovascularization, retinal neovascularization, ROP, FEVR, Coats' disease, Norrie Disease, OPPG (Osteoporosis-Pseudoglioma Syndrome), subconjunctival hemorrhage, and hypertensive retinopathy.

In certain embodiments, labeled anti-LRP5 antibodies are provided. Labels include, but are not limited to, labels or moieties that are detected directly (such as fluorescent, chromophoric, electron-dense, chemiluminescent, and radioactive labels), as well as moieties, such as enzymes or ligands, that are detected indirectly, e.g., through an enzymatic reaction or molecular interaction. Exemplary labels include, but are not limited to, the radioisotopes $^{32}P$, $^{14}C$, $^{125}I$, $^{3}H$, and $^{131}I$, fluorophores such as rare earth chelates or fluorescein and its derivatives, rhodamine and its derivatives, dansyl, umbelliferone, luceriferases, e.g., firefly luciferase and bacterial luciferase (U.S. Pat. No. 4,737,456), luciferin, 2,3-dihydrophthalazinediones, horseradish peroxidase (HRP), alkaline phosphatase, β-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor such as HRP, lactoperoxidase, or microperoxidase, biotin/avidin, spin labels, bacteriophage labels, stable free radicals, and the like.

F. Pharmaceutical Formulations

Pharmaceutical formulations of an anti-LRP5 antibody as described herein are prepared by mixing such antibody having the desired degree of purity with one or more optional pharmaceutically acceptable carriers (*Remington's Pharmaceutical Sciences* 16th edition, Osol, A. Ed. (1980)), in the form of lyophilized formulations or aqueous solutions. Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG). Exemplary pharmaceutically acceptable carriers herein further include insterstitial drug dispersion agents such as soluble neutral-active hyaluronidase glycoproteins (sHASEGP), for example, human soluble PH-20 hyaluronidase glycoproteins, such as rHuPH20 (HYLENEX®, Baxter International, Inc.). Certain exemplary sHASEGPs and methods of use, including rHuPH20, are described in US Patent Publication Nos. 2005/0260186 and 2006/0104968. In one aspect, a sHASEGP is combined with one or more additional glycosaminoglycanases such as chondroitinases.

Exemplary lyophilized antibody formulations are described in U.S. Pat. No. 6,267,958. Aqueous antibody formulations include those described in U.S. Pat. No. 6,171,586 and WO2006/044908, the latter formulations including a histidine-acetate buffer.

The formulation herein may also contain more than one active ingredients as necessary for the particular indication being treated, preferably those with complementary activities that do not adversely affect each other. For example, it may be desirable to further provide a VEGF antagonist (including, e.g., an anti-VEGF antibody or antibody fragment, e.g. ranibizumab, a soluble VEGF receptor or fragment thereof, e.g. aflibercept, or an aptamer, e.g. pegaptanib), a TSPAN12 agonist, plasmin, plasminogen, tissue plasminogen activator, triamcinolone, a TNF-α inhibitor, and/or dexamethasone. Such active ingredients are suitably present in combination in amounts that are effective for the purpose intended.

Active ingredients may be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences* 16th edition, Osol, A. Ed. (1980).

Sustained-release preparations may be prepared. Suitable examples of sustained-release preparations include semipermeable matrices of solid hydrophobic polymers containing the antibody, which matrices are in the form of shaped articles, e.g. films, or microcapsules.

The formulations to be used for in vivo administration are generally sterile. Sterility may be readily accomplished, e.g., by filtration through sterile filtration membranes.

G. Therapeutic Methods and Compositions

Any of the anti-LRP5 antibodies provided herein may be used in therapeutic methods.

In one aspect, an anti-LRP5 antibody for use as a medicament is provided. In further aspects, an anti-LRP5 antibody for use in treating retinopathies including proliferative diabetic retinopathy, CNV, AMD, diabetic and other ischemia-related retinopathies, DME, pathological myopia, von Hippel-Lindau disease, histoplasmosis of the eye, CRVO, BRVO, corneal neovascularization, retinal neovascularization, ROP, FEVR, Coats' disease, Norrie Disease, OPPG (Osteoporosis-Pseudoglioma Syndrome), subconjunctival hemorrhage, and hypertensive retinopathy is provided. In certain embodiments, an anti-LRP5 antibody for use in a method of treatment is provided. In certain embodiments, the invention provides an anti-LRP5 antibody for use in a method of treating an individual having a retinopathy including proliferative diabetic retinopathy, CNV, AMD, diabetic and other ischemia-related retinopathies, DME, pathological myopia, von Hippel-Lindau disease, histoplasmosis of the eye, CRVO, BRVO, corneal neovascularization, retinal neovascularization, ROP, FEVR, Coats' disease, Norrie Disease, OPPG (Osteoporosis-Pseudoglioma Syndrome), subconjunctival hemorrhage, or hypertensive retinopathy comprising administering to the individual an effective amount of the anti-LRP5 antibody. In one such embodiment, the method further comprises administering to the individual an effective amount of at least one additional therapeutic agent, e.g., as described below. In further embodiments, the invention provides an anti-LRP5 antibody for use in potentiating Norrin activity and/or potentiating Norrin/Fzd4 signaling. In certain embodiments, the invention provides an anti-LRP5 antibody for use in a method of potentiating Norrin activity and/or potentiating Norrin/Fzd4 signaling in an individual comprising administering to the individual an effective of the anti-LRP5 antibody to potentiate Norrin activity and/or potentiate Norrin/Fzd4 signaling. An "individual" according to any of the above embodiments is preferably a human.

In a further aspect, the invention provides for the use of an anti-LRP5 antibody in the manufacture or preparation of a medicament. In one embodiment, the medicament is for treatment of a retinopathy including proliferative diabetic retinopathy, CNV, AMD, diabetic and other ischemia-related retinopathies, DME, pathological myopia, von Hippel-Lindau disease, histoplasmosis of the eye, CRVO, BRVO, corneal neovascularization, retinal neovascularization, ROP, FEVR, Coats' disease, Norrie Disease, OPPG (Osteoporosis-Pseudoglioma Syndrome), subconjunctival hemorrhage, or hypertensive retinopathy. In a further embodiment, the medicament is for use in a method of treating a retinopathy including proliferative diabetic retinopathy, CNV, AMD, diabetic and other ischemia-related retinopathies, DME, pathological myopia, von Hippel-Lindau disease, histoplasmosis of the eye, CRVO, BRVO, corneal neovascularization, retinal neovascularization, ROP, FEVR, Coats' disease, Norrie Disease, OPPG (Osteoporosis-Pseudoglioma Syndrome), subconjunctival hemorrhage, or hypertensive retinopathy comprising administering to an individual having a retinopathy including proliferative diabetic retinopathy, CNV, AMD, diabetic and other ischemia-related retinopathies, DME, pathological myopia, von Hippel-Lindau disease, histoplasmosis of the eye, CRVO, BRVO, corneal neovascularization, retinal neovascularization, ROP, FEVR, Coats' disease, Norrie Disease, OPPG (Osteoporosis-Pseudoglioma Syndrome), subconjunctival hemorrhage, or hypertensive retinopathy an effective amount of the medicament. In one such embodiment, the method further comprises administering to the individual an effective amount of at least one additional therapeutic agent, e.g., as described below. In a further embodiment, the medicament is for potentiating Norrin activity and/or potentiating Norrin/Fzd4 signaling. In a further embodiment, the medicament is for use in a method of potentiating Norrin activity and/or potentiating Norrin/Fzd4 signaling in an individual comprising administering to the individual an amount effective of the medicament to potentiate Norrin activity and/or potentiate Norrin/Fzd4 signaling. An "individual" according to any of the above embodiments may be a human.

In a further aspect, the invention provides a method for treating a retinopathy including proliferative diabetic retinopathy, CNV, AMD, diabetic and other ischemia-related retinopathies, DME, pathological myopia, von Hippel-Lindau disease, histoplasmosis of the eye, CRVO, BRVO, corneal neovascularization, retinal neovascularization, ROP, FEVR, Coats' disease, Norrie Disease, OPPG (Osteoporosis-Pseudoglioma Syndrome), subconjunctival hemorrhage, or hypertensive retinopathy. In one embodiment, the method comprises administering to an individual having such retinopathy including proliferative diabetic retinopathy, CNV, AMD, diabetic and other ischemia-related retinopathies, DME, pathological myopia, von Hippel-Lindau disease, histoplasmosis of the eye, CRVO, BRVO, corneal neovascularization, retinal neovascularization, ROP, FEVR, Coats' disease, Norrie Disease, OPPG (Osteoporosis-Pseudoglioma Syndrome), subconjunctival hemorrhage, or hypertensive retinopathy an effective amount of an anti-LRP5 antibody. In one such embodiment, the method further comprises administering to the individual an effective amount of at least one additional therapeutic agent, as described below. An "individual" according to any of the above embodiments may be a human.

In a further aspect, the invention provides a method for potentiating Norrin activity and/or potentiating Norrin/Fzd4 signaling in an individual. In one embodiment, the method comprises administering to the individual an effective amount of an anti-LRP5 antibody to potentiate Norrin activity and/or potentiate Norrin/Fzd4 signaling. In one embodiment, an "individual" is a human.

In a further aspect, the invention provides pharmaceutical formulations comprising any of the anti-LRP5 antibodies provided herein, e.g., for use in any of the above therapeutic methods. In one embodiment, a pharmaceutical formulation comprises any of the anti-LRP5 antibodies provided herein and a pharmaceutically acceptable carrier. In another embodiment, a pharmaceutical formulation comprises any of the anti-LRP5 antibodies provided herein and at least one additional therapeutic agent, e.g., as described below.

Antibodies of the invention can be used either alone or in combination with other agents in a therapy. For instance, an antibody of the invention may be co-administered with at least one additional therapeutic agent. In certain embodiments, an additional therapeutic agent is a VEGF antagonist (including, e.g., an anti-VEGF antibody or antibody fragment, e.g. ranibizumab, a soluble VEGF receptor or fragment thereof, e.g. aflibercept, or an aptamer, e.g. pegaptanib), a TSPAN12 agonist, plasmin, plasminogen, tissue plasminogen activator, triamcinolone, a TNF-α inhibitor, and/or dexamethasone.

Such combination therapies noted above encompass combined administration (where two or more therapeutic agents are included in the same or separate formulations), and separate administration, in which case, administration of the antibody of the invention can occur prior to, simultaneously, and/or following, administration of the additional therapeutic agent and/or adjuvant.

An antibody of the invention (and any additional therapeutic agent) can be administered by any suitable means, including parenteral, intrapulmonary, and intranasal, and, if desired for local treatment, intraocular administration (e.g. intravitreal administration). Parenteral infusions include intramuscular, intravenous, intraarterial, intraperitoneal, or subcutaneous administration. Dosing can be by any suitable route, e.g. by injections, such as intravitreal, depending in part on whether the administration is brief or chronic. Various dosing schedules including but not limited to single or multiple administrations over various time-points, bolus administration, and pulse infusion are contemplated herein.

Antibodies of the invention would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The antibody need not be, but is optionally formulated with one or more agents currently used to prevent or treat the disorder in question. The effective amount of such other agents depends on the amount of antibody present in the formulation, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

For the prevention or treatment of disease, the appropriate dosage of an antibody of the invention (when used alone or in combination with one or more other additional therapeutic agents) will depend on the type of disease to be treated, the type of antibody, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatments. Depending on the type and severity of the disease, about 1 µg/kg to 15 mg/kg (e.g. 0.1 mg/kg-10 mg/kg) of antibody can be an initial candidate dosage for administration to the patient, whether, for example, by one or more separate administrations, or by continuous infusion. One typical daily dosage might range from about 1 µg/kg to 100 mg/kg or more, depending on the factors mentioned above. For repeated administrations over several days or longer, depending on the condition, the treatment would generally be sustained until a desired suppression of disease symptoms occurs. One exemplary dosage of the antibody would be in the range from about 0.05 mg/kg to about 10 mg/kg. Thus, one or more doses of about 0.5 mg/kg, 2.0 mg/kg, 4.0 mg/kg or 10 mg/kg (or any combination thereof) may be administered to the patient. Such doses may be administered intermittently, e.g. every week or every three weeks (e.g. such that the patient receives from about two to about twenty, or e.g. about six doses of the antibody). An initial higher loading dose, followed by one or more lower doses may be administered. However, other dosage regimens may be useful. The progress of this therapy is easily monitored by conventional techniques and assays.

It is understood that any of the above formulations or therapeutic methods may be carried out using an immunoconjugate of the invention in place of or in addition to an anti-LRP5 antibody.

H. Articles of Manufacture

In another aspect of the invention, an article of manufacture containing materials useful for the treatment, prevention and/or diagnosis of the disorders described above is provided. The article of manufacture comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the condition and may have a sterile access port (for example the container may be an intravenous solution bag or a vial having a stopper pierceable by a hypodermic injection needle). At least one active agent in the composition is an antibody of the invention. The label or package insert indicates that the composition is used for treating the condition of choice. Moreover, the article of manufacture may comprise (a) a first container with a composition contained therein, wherein the composition comprises an antibody of the invention; and (b) a second container with a composition contained therein, wherein the composition comprises a further cytotoxic or otherwise therapeutic agent. The article of manufacture in this embodiment of the invention may further comprise a package insert indicating that the compositions can be used to treat a particular condition. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

It is understood that any of the above articles of manufacture may include an immunoconjugate of the invention in place of or in addition to an anti-LRP5 antibody.

III. Examples

The following are examples of methods and compositions of the invention. It is understood that various other embodiments may be practiced, given the general description provided above.

Example 1

Generation of Anti-LRP5 Antibodies

Library Sorting and Screening to Identify Anti-LRP5-E3/E4 Antibodies

We generated several LRP5 expression constructs, including those encoding the entire extracellular region, all four β-propeller domains E1-4, each β-propeller domain alone, and E3-E4, and found that only the clone encoding the E3-E4 domains produced a significant quantity of soluble expressed protein. Therefore, we used biotinylated human LRP5 domains E3-E4 generated in-house (E644-Q1263 of SEQ ID NO: 42) as antigen for library sorting. Nunc 96 well Maxisorp® immunoplates were coated overnight at 4° C. with NeutrAvidin® (Fisher Scientific, #89890, 10 μg/ml) or streptavidin (Fisher Scientific, #21125, 10 μg/ml) and were blocked for 1 hour at room temperature with phage blocking buffer PBST (phosphate-buffered saline (PBS) and 1% (w/v) bovine serum albumin (BSA) and 0.05% (v/v) tween-20). Biotinylated LRP5-E3/E4 (10 μg/ml) was then captured onto the plate by NeutrAvidin®/streptavidin for 1 hour at room temperature. Synthetic phage libraries of human antibodies (see, e.g., Lee et al., J. Immunol. Meth. 284:119-132, 2004, Liang et al., J. Molec. Biol. 366: 815-829, 2007) were added to antigen plates separately and incubated overnight at room temperature. The following day antigen-coated plates were washed ten times with PBT (PBS with 0.05% Tween® 20), and bound phage were eluted with 50 mM HCl and 500 mM NaCl for 30 minutes and neutralized with an equal volume of 1 M Tris base (pH7.5). Recovered phages were amplified in E. coli XL-1 Blue cells. During the subsequent selection rounds, incubation of antibody phage with the antigen-coated plates was reduced to 2-3 hours, and the stringency of plate washing was gradually increased.

After 6 rounds of panning, significant enrichment was observed. 96 clones were picked each from library track to determine whether they specifically bind to human LRP5E3/E4. The variable regions of these clones were PCR sequenced to identify unique sequence clones.

The phage supernatant was diluted 1:5 in ELISA (enzyme linked immunosorbent assay) buffer (PBS with 0.5% BSA, 0.05% Tween® 20) in 100 μl total volume and was transferred to the target protein coated plates (1 μg/ml LRP5E3/E4 directly coated overnight) or neutravidin/streptavidin coated plate (5 μg/ml of each protein). The plate was gently shaken for 1 hour to allow phage to bind to the protein-coated plates. The plate was washed ten times with PBS-0.05% Tween® 20. The binding was quantified by adding horseradish peroxidase (HRP)-conjugated anti-M13 antibody in ELISA buffer (1:5000) and incubated for 30 minutes at room temperature. The plates were washed ten times with PBS-0.05% Tween® 20. Next, 100 μl/well of a 1:1 ratio of 3,3',5,5'-tetramethylbenzidine (TMB) Peroxidase substrate and Peroxidase Solution B ($H_2O_2$) (Kirkegaard-Perry Laboratories (Gaithersburg, Md.)) was added to the well and incubated for 5 minutes at room temperature. The reaction was stopped by adding 100 μl 0.1M phosphoric Acid ($H_3PO_4$) to each well and allowed to incubate for 5 minutes at room temperature. The OD (optical density) of the yellow color in each well was determined using a standard ELISA plate reader at 450 nm. The OD reduction (%) was calculated by the following equation:

$$OD_{450nm} \text{ reduction (\%)}=[(OD_{450nm} \text{ of wells with competitor})/(OD_{450nm} \text{ of well with no competitor})]*100$$

Clones that had the $OD_{450nm}$ at least 5 fold higher to LRP5E3/E4 than background were picked and reformatted into full length human IgG1 by cloning $V_L$ and $V_H$ regions of individual clones into the LPG3 and LPG4 vector respectively. These clones were subsequently transiently expressed in mammalian CHO cells, and purified with a protein A column.

Construct Libraries and Panning Strategy for Affinity Improvement of Clones Derived from the Synthetic Phage Libraries For each clone that showed promising cell-based assay activity, YW629.42 and YW629.51, phagemid containing 4 stop codons (TAA) in CDR L3 and displaying monovalent Fab on the surface of M13 bacteriophage was generated. These phagemids served as the templates for Kunkel mutagenesis for the construction of affinity maturation libraries.

For affinity maturation, soft randomization strategy was used, where mutagenic DNA was synthesized with 70-10-10-10 mixtures of bases favoring the wild type nucleotides to obtain the mutation rate of approximately 50% at the selected positions (Gallop et al., *Journal of Medicinal Chemistry* 37:1233-1251 (1994)). Four different combinations of CDR loops, H1/L3, H2/L3, H3/L3, and L1/L2/L3 were selected for randomization.

For affinity improvement selection, in-house generated LRP5E3/E4 was first biotinylated under limiting reagent condition. Phage libraries were subjected to six rounds of solution sorting with increasing stringency. For the first round of solution sorting, 3 O.D./ml in 1% BSA and 0.05% Tween® 20 of phage input were incubated to plates pre-coated with LRP5E3/E4 for 3 hours. The wells were washed with PBS-0.05% Tween® 20 ten times. Bound phage was eluted with 150 µl/well 50 mM HCl, 500 mM KCl for 30 minutes, and subsequently neutralized by 50 µl/well of 1M Tris pH8, titered, and propagated for the next round. For subsequent rounds, panning of the phage libraries was done in solution phase, where phage library was incubated with initial concentration of 100 nM biotinylated target protein (the concentration is based on parental clone phage IC50 value) in 100 µl SuperBlock buffer (Pierce Biotechnology) for 2 hours at room temperature. The mixture was further diluted 10× with SuperBlock, and 100 µl/well was applied to NeutrAvidin®-coated wells (10 µg/ml) for 30 minutes at room temperature with gentle shaking To determine background binding, control wells containing phage were captured on neutravidin-coated plates. Bound phage was then washed, eluted and propagated as described for first round. Five more rounds of solution sorting were carried out together with increasing selection stringency. The first couple rounds of which is for on-rate selection by decreasing biotinylated target protein concentration from 100 nM to 0.5 nM, and the last two rounds of which is for off-rate selection by adding excess amounts of non-biotinylated target protein (300 to 1000 fold more) to compete off weaker binders at room temperature.

High Throughput Affinity Screening ELISA (Single Spot Competition)

Colonies were picked from the sixth round of panning for screening. Colonies were grown overnight at 37° C. in 1 ml/well of 2YT media with 50 µg/ml carbenicillin and 1×10$^{10}$/ml M13KO7 in 96-well plate (Falcon). From the same plate, a colony of XL-1 infected parental phage was included as control. 96-well Nunc Maxisorp® plates were coated with 100 µl/well of LRP5E3/E4 (0.5 µg/ml) in PBS at 4° C. overnight. The plates were blocked with 150 µl of 1% BSA and 0.05% Tween® 20 in PBS 20 for 1 hour.

Figure 5B:
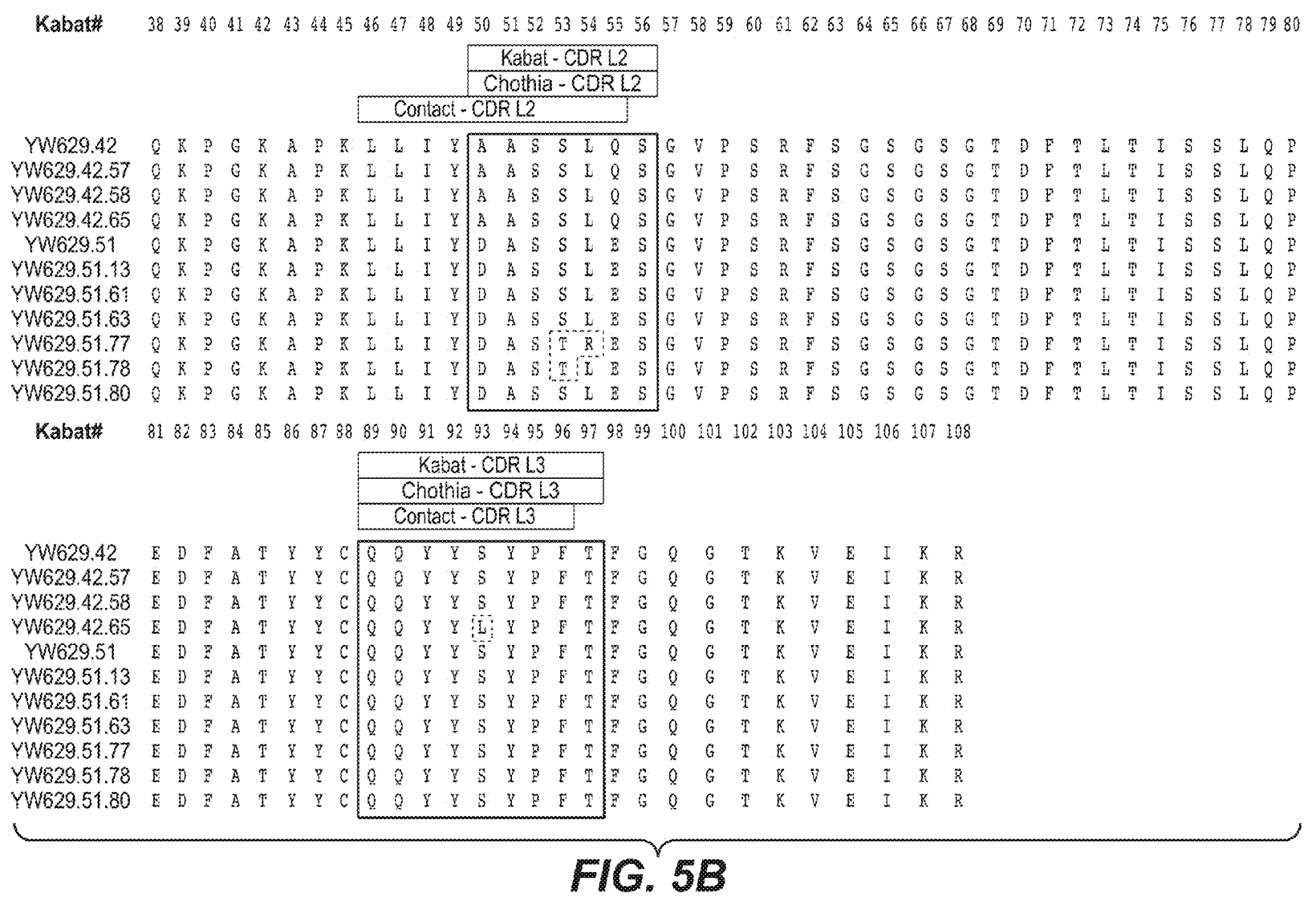

35 µl of the phage supernatant was diluted with to 75 µl of in ELISA (enzyme linked immunosorbent assay) buffer (PBS with 0.5% BSA, 0.05% Tween® 20) with or without 5 nM LRP5E3/4 and let incubate for 1 hour at room temperature in an F plate (NUNC). 95 µl of mixture was transferred side by side to the antigen-coated plates. The plate was gently shaken for 15 min and was washed ten times with PBS-0.05% Tween® 20. The binding was quantified by adding horseradish peroxidase (HRP)-conjugated anti-M13 antibody in ELISA buffer (1:2500) and incubated for 30 minutes at room temperature. The plates were washed with PBS-0.05% Tween® 20 ten times. Next, 100 µl/well of Peroxidase substrate was added to the well and incubated for 5 minutes at room temperature. The reaction was stopped by adding 100 µl 0.1M Phosphoric Acid ($H_3PO_4$) to each well and allowed to incubate for 5 minutes at room temperature. The O.D. (optical density) of each well was determined using a standard ELISA plate reader at 450 nm. In comparison to the $OD_{450nm}$ reduction (%) of the well of parental phage (100%), clones that had the $OD_{450nm}$ reduction (%) lower than 50% were picked for sequence analysis. Unique clones were selected for phage preparation to determine binding affinity (phage IC50) against target antigen LRP5E3/E4 by comparison to parental clone. Clone that showed most affinity-improvement were reformatted into human IgG1 for antibody production and further BIAcore™ binding kinetic analysis and other in vitro or in vivo assays. The variable domain sequences for certain antibodies that were identified by this process are shown in FIGS. 4 and 5. In this specification the prefixes "YW629" and "P6C" may be used interchangeably. Therefore, e.g., the antibody described as YW629.51.61 is the same as P6C.51.61.

Characterization of Anti-LRP5 Antibodies (BIAcore)

Binding affinities of anti-LRP5E3/E4 IgGs were measured by Surface Plasmon Resonance (SPR) using a BIAcore™-T100 instrument. Anti-LRP5E3/E4 human IgGs were captured by mouse anti-human Fc antibody (GE Healthcare, cat# BR-1008-39) coated on CM5 biosensor chips to achieve approximately 200 response units (RU). For kinetics measurements, two-fold serial dilutions (500 nM to 0.245 nM) of human LRP5E3/E4 (GNE) were injected in HBS-P buffer (10 mM HEPES, pH 7.4, 0.15 M NaCl, 0.005% surfactant P20) at 25° C. with a flow rate of 30 µl/min. Association rates ($k_{on}$) and dissociation rates ($k_{off}$) were calculated using a simple one-to-one Langmuir binding model (BIAcore Evaluation Software version 2.0.2). The equilibrium dissociation constant ($K_D$) was calculated as the ratio $k_{off}/k_{on}$. The results of this analysis for the antibodies in FIGS. 4 and 5 are shown in Table 2 below.

TABLE 2

BIAcore analysis of anti-LRP5 antibodies

| Ligand | ka (1/Ms) | kd (1/s) | KD (M) |
| --- | --- | --- | --- |
| YW629.42 | 2.26 × 10$^4$ | 1.16 × 10$^{-3}$ | 5.16 × 10$^{-8}$ |
| YW629.42.57 | 3.01 × 10$^4$ | 1.63 × 10$^{-4}$ | 5.42 × 10$^{-9}$ |
| YW629.42.58 | 3.13 × 10$^4$ | 8.69 × 10$^{-5}$ | 2.78 × 10$^{-9}$ |
| YW629.42.65 | 3.79 × 10$^4$ | 9.63 × 10$^{-5}$ | 2.54 × 10$^{-9}$ |
| YW629.51 | 2.37 × 10$^5$ | 3.09 × 10$^{-3}$ | 1.30 × 10$^{-8}$ |
| YW629.51.13 | 3.27 × 10$^5$ | 3.69 × 10$^{-4}$ | 1.13 × 10$^{-9}$ |
| YW629.51.61 | 2.44 × 10$^5$ | 1.15 × 10$^{-4}$ | 4.70 × 10$^{-10}$ |
| YW629.51.63 | 3.37 × 10$^5$ | 1.99 × 10$^{-4}$ | 5.92 × 10$^{-10}$ |
| YW629.51.77 | 3.76 × 10$^5$ | 1.65 × 10$^{-4}$ | 4.38 × 10$^{-10}$ |
| YW629.51.78 | 3.78 × 10$^5$ | 7.24 × 10$^{-5}$ | 1.92 × 10$^{-10}$ |
| YW629.51.80 | 3.87 × 10$^5$ | 1.04 × 10$^{-4}$ | 2.68 × 10$^{-10}$ |

Example 2

Identification of Antibodies with Norrin Pathway Potentiating Activity

Norrin signals through a membrane complex comprising LRP5, Frizzled4 (FZD4) and Tetraspanin12 (TSPAN12). Mutants have been identified in each of Norrin (e.g. Norrin-C95R), FZD4 (e.g. FZD4-M157V) and TSPAN12 (e.g. TSPAN12-G188R), which exhibit signaling deficiencies. We tested the ability of various LRP5 antibodies to impact Norrin-mediated signaling.

Figure 1B:
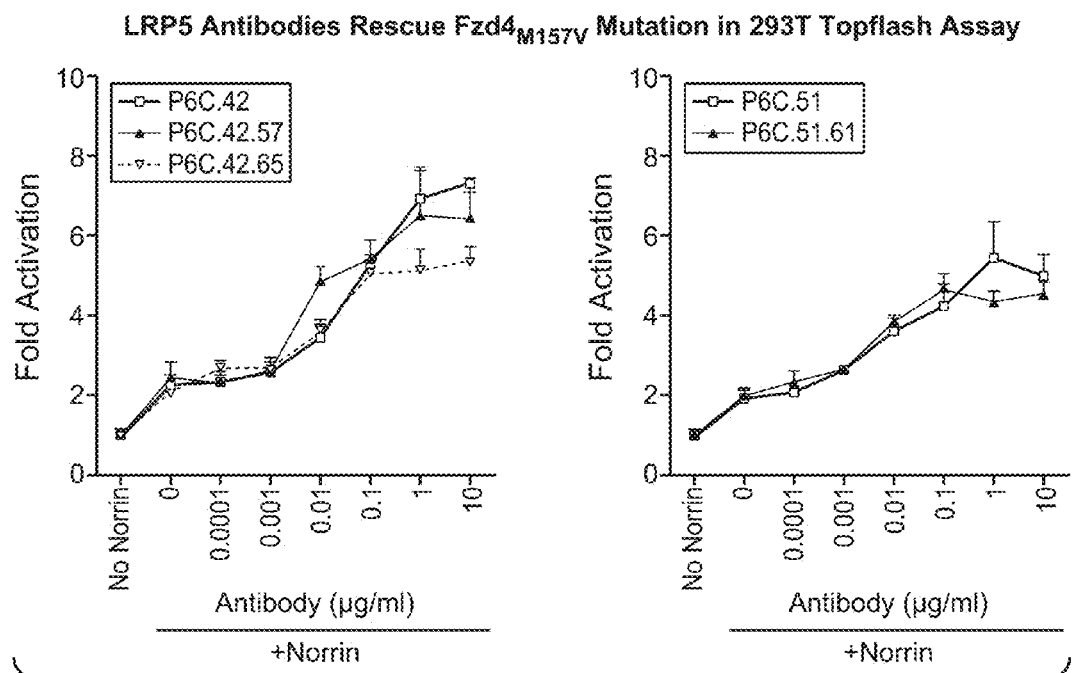

In 24-well plates, 1.6×10$^5$ cells/well were transfected with DNA mix containing b-Catenin reporter mix (TOPFlash, pRL-CMV, and pCan-myc-lef-1), LRP5, and Fzd4 or Fzd4-M157V. Twenty-four hours following transfection, the indicated amount of each LRP5 antibody was added. One hour later, 125 ng/ml of recombinant Norrin was added to wells as indicated. Following an additional 16-hour incubation at 37° C., cells were lysed and Firefly and Renilla luciferase expression was measured using Promega Dual-Glo® Reagents. Firefly luciferase values were normalized to Renilla expression. Norrin activates reporter gene expression by ~5-fold relative to no ligand. Addition of increasing amounts of antibody potentiates Norrin activity to ~10-fold at 0.1-1 µg/ml in all antibodies tested (FIG. 1A). When Fzd4-M157V is substituted for Fzd4 in the transfection, Norrin activation is reduced to only 2-fold. Addition of LRP5 antibodies rescues defective signaling to levels mirroring wildtype Fzd4 (FIG. 1B). These data indicate that anti-LRP5 antibodies potentiate Norrin/Fzd4 signaling and rescue the Fzd4-M157V mutation.

Figure 2A:
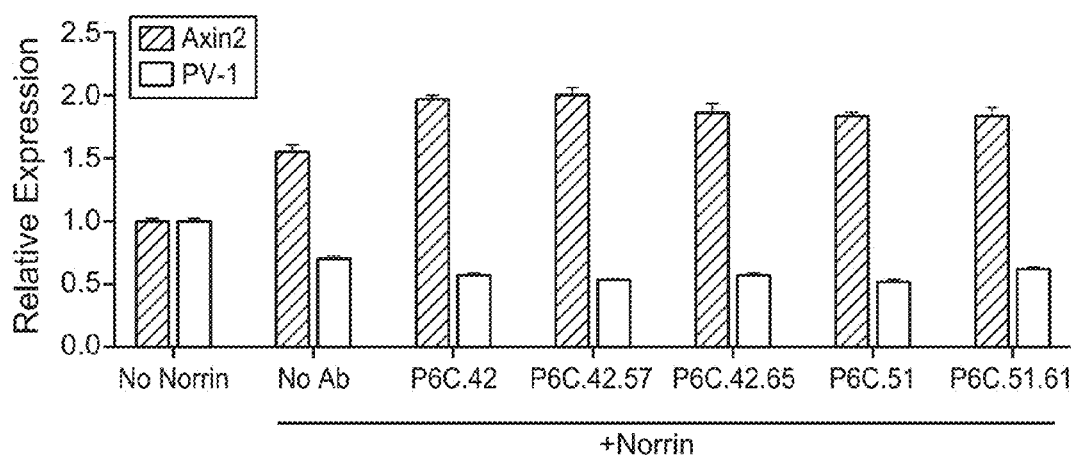
FIGS. 2A and 2B show that anti-LRP5 antibodies potentiate Norrin activity and rescue loss of Tspan12 in human retinal endothelial microvascular cells (HREMVC). In this Figure the prefix "P6C" is used, whereas in other places in the specification "YW629" is used interchangeably.
Figure 2B:
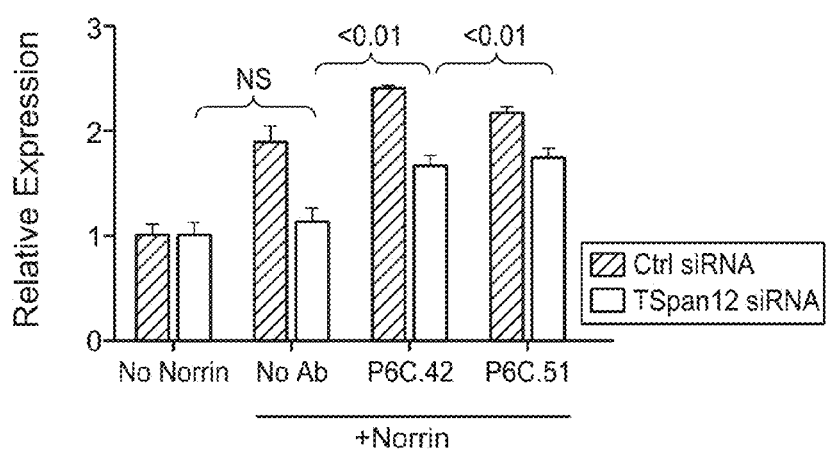

$3 \times 10^5$ human retinal endothelial microvascular cells (HREMVC) were seeded on a 6-well dish. The next day 10 µg/ml of the indicated antibody was added, followed by 1.25 µg/ml Norrin, one-hour later. After an additional 24-hours the RNA was isolated for Q-PCR analysis of Norrin target genes, PV-1 (down-regulated by Norrin) and Axin-2 (up-regulated by Norrin). Addition of Norrin upregulates Axin-2 expression by ~1.6-fold and downregulates PV-1 by ~0.7-fold, relative to no ligand. Addition of indicated LRP5 antibodies further upregulates Axin-2 to ~2-fold and down-regulates PV-1 to ~0.5-fold (FIG. 2A). $3 \times 10^5$ HREMVC were seeded on 6-well dishes. Once cells were attached (~4-hours), they were transfected with 100 nM control or Tspan12 siRNA using DharmaFECT® transfection reagent. The following day the cells were seeded into a 24-well plate and treated with indicated antibody and ligand (as above). As indicated by measuring Axin-2 gene expression, knockdown of Tspan12 prevents activation with Norrin. Addition of 10 µg/ml of the indicated LRP-5 antibodies partially rescues this defective Norrin signaling (FIG. 2B). These data indicate that LRP5 antibodies potentiate Norrin activity and rescue loss of Tspan12.

Figure 3A:
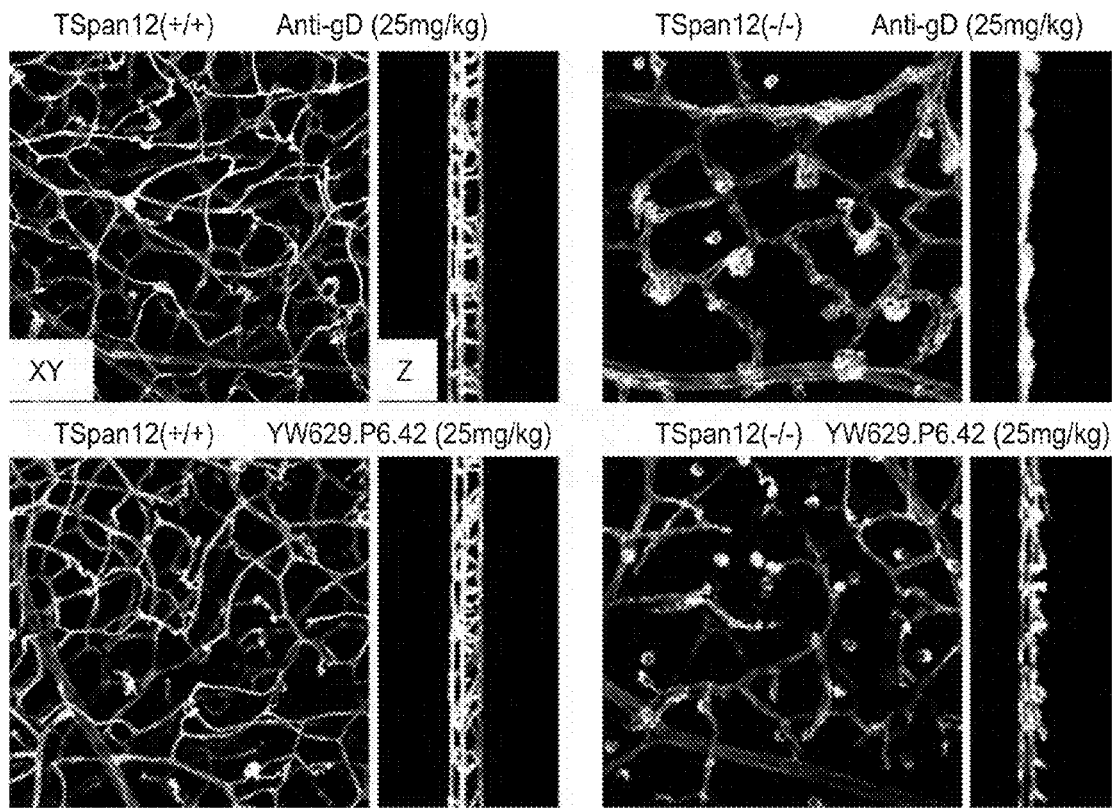
FIGS. 3A and 3B show that an anti-LRP5 antibody partially rescues vascular defects in Tspan12 knockout mice. In this Figure the prefix "P6C" is used, whereas in other places in the specification "YW629" is used interchangeably.
Figure 3B:
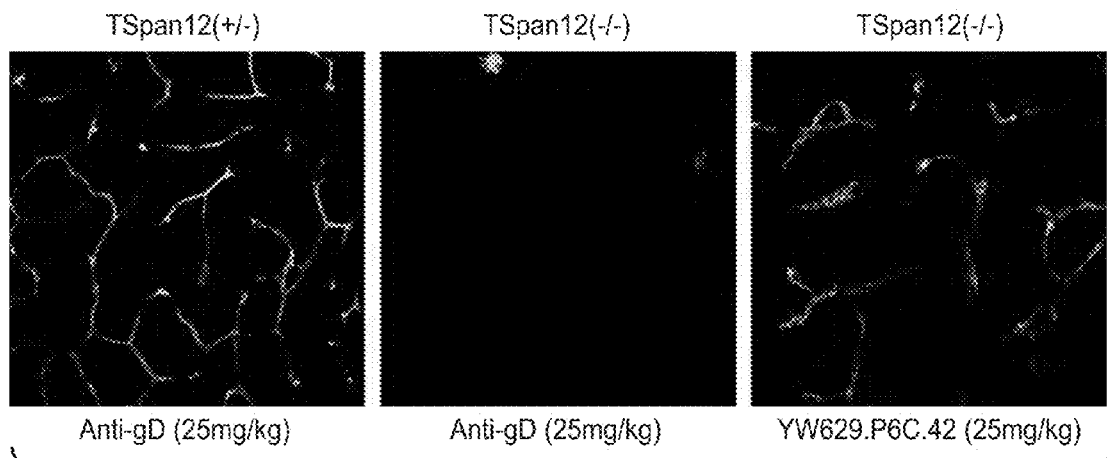

We next test the activity of the anti-LRP5 antibodies in vivo. Tspan12 knockout (KO) and wild-type littermates were treated with 25 mg/kg anti-gD (negative control antibody) or anti-LRP5 antibody (YW629.42) daily from P3-P14. On P15, the eyes were enucleated and retinas were harvested for vascular staining with biotinylated isolectin B4. Retinas were stained with streptavidin-AF488, wholemounted, and imaged using confocal microscopy. XY and Z projections were compiled from 1.6 micron stacks captured through the thickness of each retina. As expected, Tspan12 KO retina vessels stall in the superficial vascular plexus and form small pathological vascular clusters just below the ganglion cell layer. Treatment with P6C.42, but not control antibody anti-gD, partially rescues the Tspan12 KO vascular defect by promoting deep layer vascularization and reducing abnormal vascular clustering (FIG. 3A). At P15, Tspan12 KO mice fail to form an inner plexiform (IPL) vascular bed that is typical in wildtype mice. Treatment with YW629.42 partially restores the IPL vasculature as compared to similar region in anti-gD treated mice. (n=3 animals/treatment group; FIG. 3B). These data demonstrate that an anti-LRP5 antibody partially rescues vascular defects in the Tspan12 knockout mice in vivo.

Figure 6A:
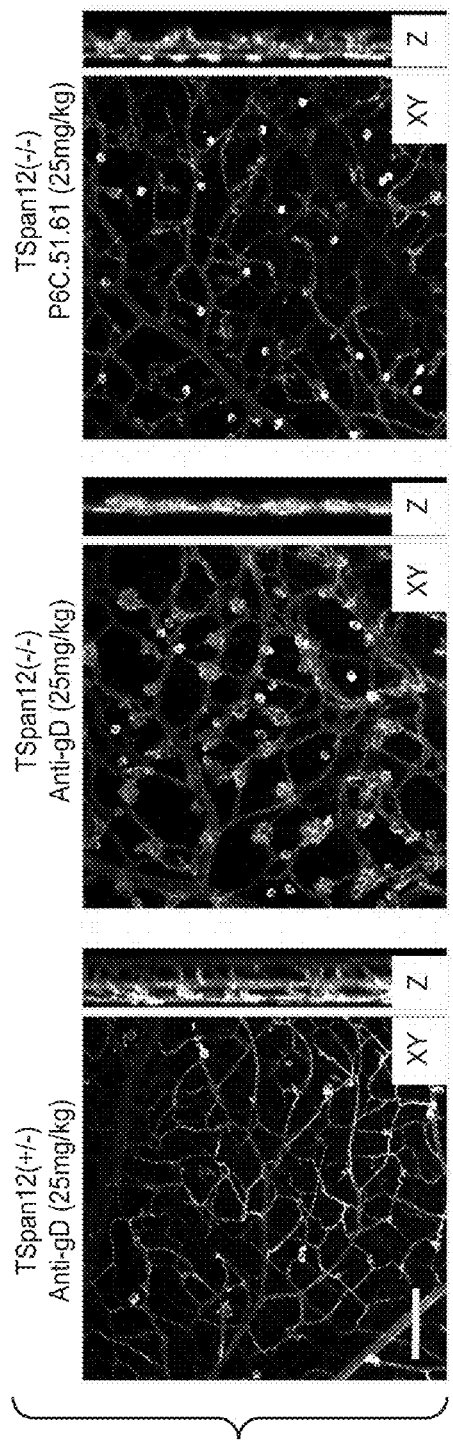
FIGS. 6A and 6B show that an anti-LRP5 antibody partially rescues retinal vascular defects associated with Tspan12 knockout.
Figure 6B:
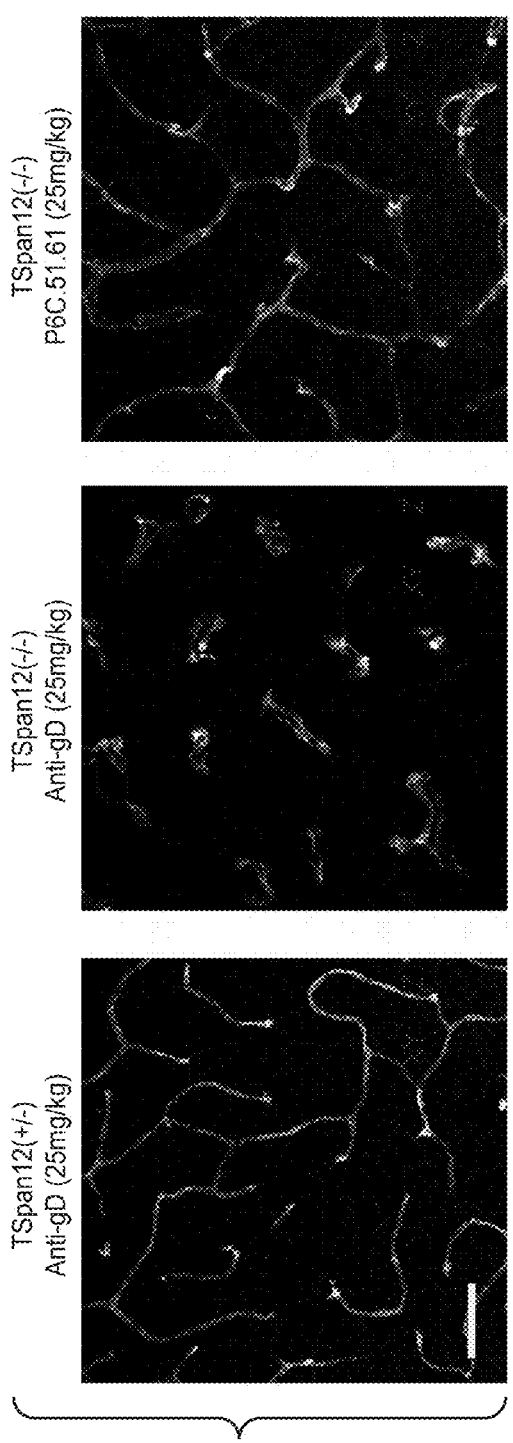

Tspan12 KO and heterozygous littermates were also treated with 25 mg/kg anti-gD or anti-LRP5 antibody (P6C.51.61). For data shown in FIG. 6A, mice were treated daily from P6-P15 and sacrificed on P16 (6 mice/treatment group). The eyes were enucleated and retinas were harvested for vascular staining with biotinylated isolectin B4. Retinas were stained with streptavidin-AF488, wholemounted, and imaged using confocal microscopy. XY and Z projections were compiled from 1.6 micron stacks captured through the thickness of each retina. Tspan12+/− mice display a normal retinal vasculature consisting of three distinct vascular layers (FIG. 6A, left, scale bar 100 µm). As expected, retina vessels from Tspan12−/− mice, treated with control antibody anti-gD, stall in the superficial vascular plexus and form small pathological vascular clusters below the ganglion cell layer (FIG. 6A, center). Treatment with P6C.51.61 partially rescues the Tspan12 vascular defect by promoting deep layer vascularization and reducing abnormal vascular clustering (FIG. 6A, right). For the data shown in FIG. 6B, mice were treated daily from P3-P15, followed by every other day from P15-P30 (8 mice/treatment group). At P31, eyes were enucleated and retinas were harvested and treated as described above. Vessels in the inner plexiform layer (IPL) was imaged by confocal microscopy. The IPL of Tspan12+/− mice contains the typical healthy capillary network (FIG. 6B, left, scale bar 50 µm), whereas Tspan12−/− treated with anti-gD control antibody fails to form a capillary network and develops abnormal vessel fragments in the IPL (FIG. 6B, center). Treatment with P6C.51.61 partially restores the formation of capillary network in the IPL (FIG. 6B, right).

Figure 7A:
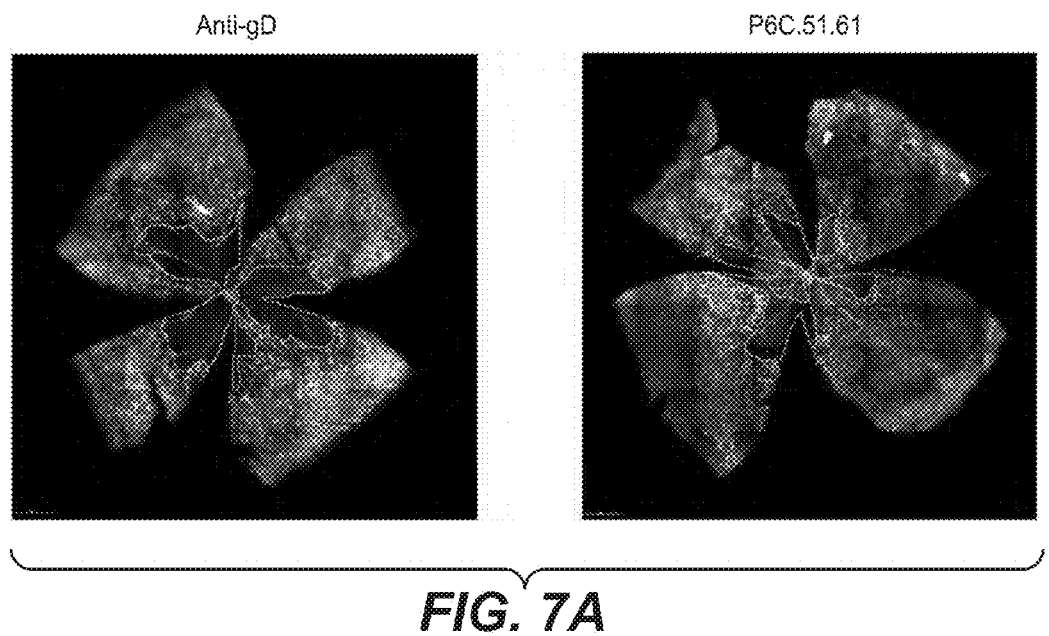
FIGS. 7A-7C show that an anti-LRP5 antibody promotes vascular regrowth and reduces pathologic angiogenesis in the oxygen induced retinopathy model of vascular retinal disease.
Figure 7B:
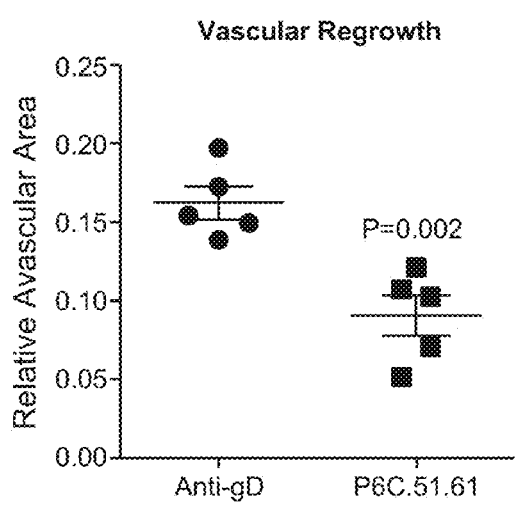
Figure 7C:
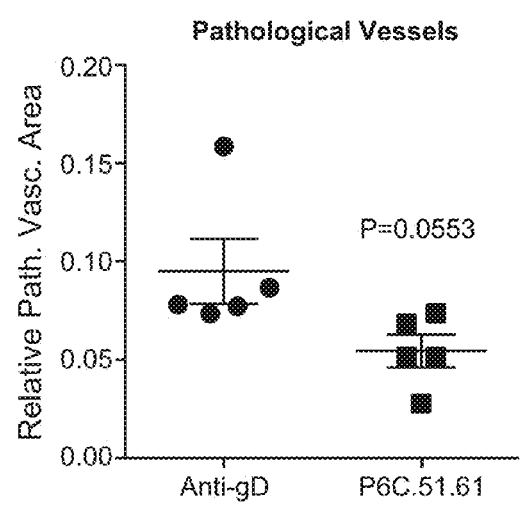

We next tested anti-LRP5 antibodies in an oxygen-induced retinopathy (OIR) model, which recapitulates certain pathologic features of adult retinal vascular disorders, such as capillary dropout and pathologic angiogenesis in retinal vein occlusion and diabetic retinopathy. The model consists of 2 phases: a hyperoxic phase from postnatal days 7-12 (P7-P12) that results in vasoobliteration in the central retina, and a relative hypoxic phase from P12-P17 that leads to pathologic angiogenesis. Briefly, during phase 1, P7 neonatal mice are placed in a hyperoxic chamber consisting of 75% oxygen for 5 days. During this phase the existing retinal vasculature regresses, resulting in a vasoobliteration around the optic nerve head at the center. During the second phase, P12 mice are raised in room air consisting of 20% oxygen. The central vasoobliteration leads to a hypoxic response that causes pathologic angiogenesis. For data shown in FIG. 7A, C57B16/N mice were subjected to the OIR procedure as described above. Mice were treated with 25 mg/kg of anti-gD (negative control antibody) or anti-LRP5 antibody (PC6.51.61) daily from P12-P17. On P17, the eyes were enucleated and retinas were harvested and stained with isolectin B4 as described previously. The total retinal area, the vasoobliterated area (outlined in center), and the pathological vasculature were measured using Fiji imaging software. FIG. 7B shows analysis of the data and despite the fact that there was no significant difference in the overall area of the retina between treatment group, mice treated with P6C.51.61 had significantly greater vascular regrowth within the vasoobliterated area than anti-gD treated littermates. FIG. 7C shows that the enhanced vascular regrowth in the P6C.51.61 treated animals was accompanied by a trend towards reduced pathological vessel formation relative to the anti-gD treated cohort. n=5 animals/treatment group.

Example 3

Analysis of Norrin Pathway Potentiating Activity of Anti-LRP5 Antibodies

Figure 8A:
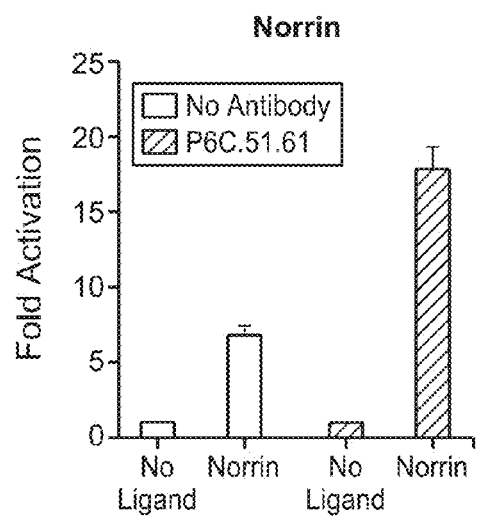
FIGS. 8A-8C show that an anti-LRP5 antibody potentiates Norrin and Wnt7b signaling, but while antagonizing Wnt3a signaling.

We performed experiments to understand the mechanism by which our anti-LRP5 antibodies act on the Norrin pathway and its other components. In 24-well plates, $1.6 \times 10^5$ cells/well were transfected with a mixture of DNAs containing TOPFlash, pRL-CMV, and pCan-myc-lef-1, LRP5, FZD-4, and cDNA encoding the indicated ligands (Norrin, or Wnt7b, or Wnt3a). Sixteen hours after transfection, 10 µg/ml of P6C.61.51 antibody was added. Following an additional 16-hour incubation at 37° C., cells were lysed and Firefly and Renilla luciferase expression was measured using Promega Dual-Glo® Reagents. Firefly luciferase values were normalized to Renilla expression. FIG. 8A shows that Norrin activates reporter gene expression by ~6-fold relative to no ligand and that addition of 10 µg/ml of P6C.51.61 potentiates Norrin activity by 3-fold relative to Norrin alone. FIG. 7B shows experiments demonstrating that Wnt7b activates luciferase expression by ~20-fold in the absence of antibody and 2-fold enhancement over Wnt7b by P6C.51.61. FIG. 7C shows that the presence of Wnt3a activates luciferase expression by >40-fold in the absence of antibody but this activity is significantly antagonized in the presence of P6C.51.61. Taken together, these data show that P6C.51.61 potentiates Norrin and Wnt7b signaling, but antagonizes Wnt3a signaling.

Figure 8B:
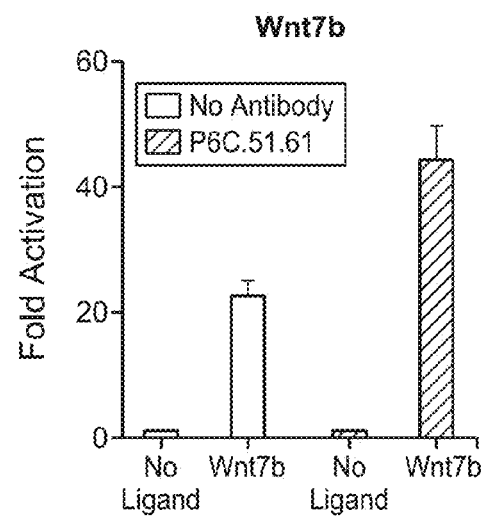
Figure 8C:
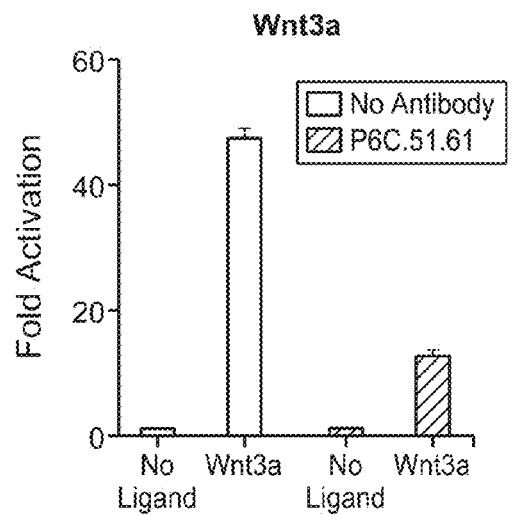
Figure 9A:
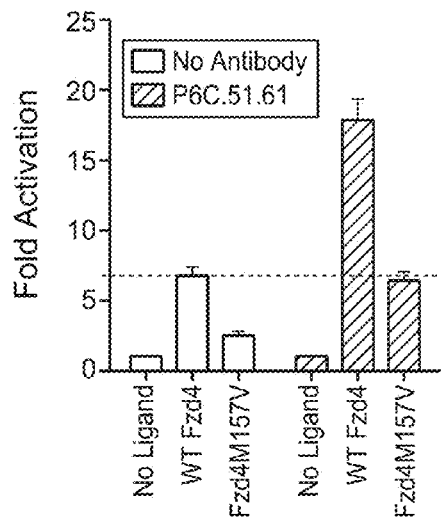
FIGS. 9A and 9B show that an anti-LRP5 antibody rescues the signaling defect of mutations in ligand or receptor component that reduce receptor clustering.
Figure 9B:
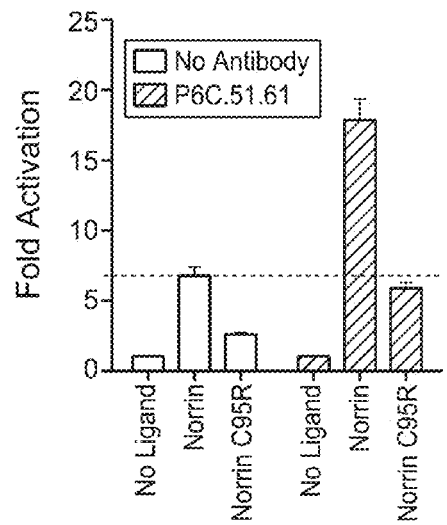

Fzd4$_{M157V}$ and Norrin$_{C95R}$ are mutations that occur in patients with FEVR spectrum disorders and these mutations lead to decreased clustering in the Fzd4/LRP5/Norrin receptor complex (Junge et al. Cell 139:299-311 (2009)). Junge et al. demonstrated that overexpression of TSPAN12 could rescue the clustering defects associated with Fzd4$_{M157V}$ and Norrin$_{C95R}$ and restore signaling to wildtype levels. We tested whether P6C.51.61 could cluster the receptor complex and similarly rescue these mutations. In 24-well plates, 1.6×10$^5$ cells/well were transfected with a mixture of DNAs containing TOPFlash, pRL-CMV, pCan-myc-lef-1, LRP5, Fzd4 or FZD4M157V, and Norrin or Norrin$_{C95R}$. Sixteen hours after transfection, 10 µg/ml of P6C.61.51 antibody was added as indicated. Following an additional 16-hour incubation at 37° C., cells were lysed and Firefly and Renilla luciferase expression was measured using Promega Dual-Glo® Reagents. Firefly luciferase values were normalized to Renilla expression. FIG. 8A shows that Norrin activates reporter gene expression by ~6-fold relative to no ligand in the presence of wild type Fzd4. Under these conditions, addition of 10 µg/ml of P6C.51.61 potentiates Norrin activity by 3-fold relative to Norrin alone. When Fzd4$_{M157V}$ is substituted for Fzd4 in the transfection, Norrin activation is reduced to ~2-fold relative to no ligand. Addition of P6C.51.61 rescues the defective Fzd4$_{M157V}$ signaling to levels mirroring wildtype Fzd4 (dotted line). FIG. 8B shows that replacing Norrin with Norrin$_{C95R}$ leads to a significant decrease in pathway activation in the absence of antibody but in the presence of P6C.51.61, Norrin$_{C95R}$ activity is restored to the level associated with wildtype Norrin (dotted line). These results demonstrate that P6C.51.61 rescues mutations in receptor components that reduce receptor clustering.

Figure 10A:
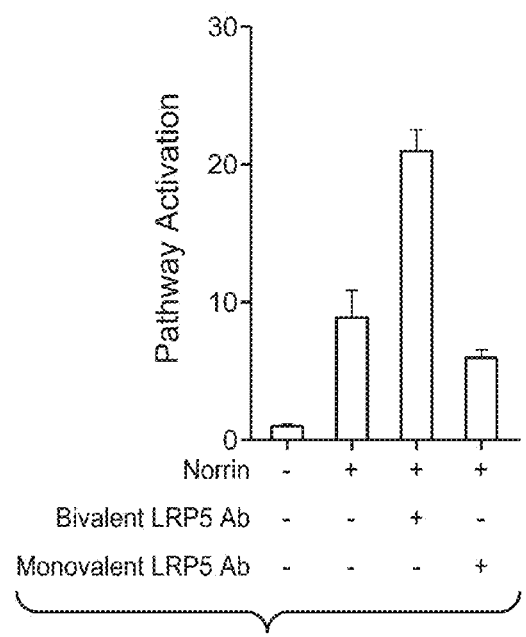
FIGS. 10A and 10B show that antibody bivalency is required for anti-LRP5 antibody-mediated potentiation of Norrin signaling, but not inhibition of Wnt3a signaling.
Figure 10B:
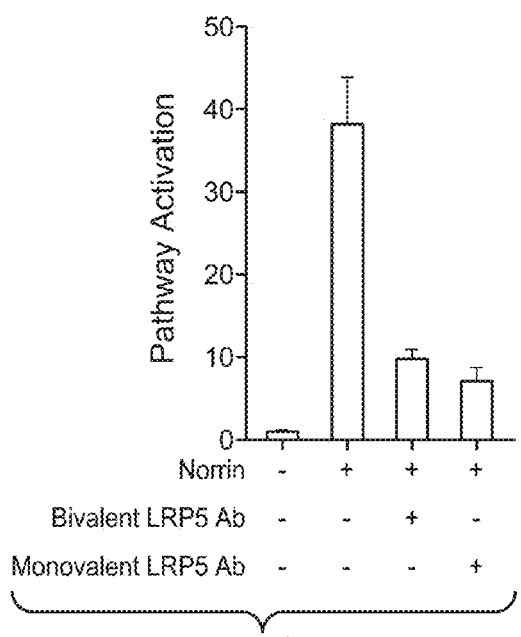

We next tested the impact of antibody valency of activity. We found that bivalent binding is required for anti-LRP5 potentiation of Norrin signaling, but not inhibition of Wnt3a signaling. In 24-well plates, 1.6×10$^5$ cells/well were transfected with a mixture of DNAs containing TOPFlash, pRL-CMV, and pCan-myc-lef-1, LRP5, and FZD-4. Twenty-four hours following transfection, the indicated amount of each LRP5 antibody was added. One hour later, 125 ng/ml of recombinant Norrin or 200 ng/ml of Wnt3a was added. Following an additional 16-hour incubation at 37° C., cells were lysed and Firefly and Renilla luciferase expression was measured using Promega Dual-Glo® Reagents. Firefly luciferase values were normalized to Renilla expression. FIG. 10A shows that Norrin activates reporter gene expression by ~8-fold relative to the control without ligand. Addition of 10 µg/ml of bivalent LRP5 antibody (P6C.51) potentiates Norrin activity by >2 fold but addition of 10 µg/ml of monovalent (Fab) LRP5 antibody fails to potentiate Norrin signaling. FIG. 10B shows that anti-LRP5 antibody antagonizes Wnt3a signaling in the presence of 10 µg/ml of either bivalent or monovalent LRP5. These data suggest that the bivalent nature of the anti-LRP5 MAb is required for clustering of the receptor complex, which is known to be required for Norrin signaling.

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

What is claimed is:

1. An isolated nucleic acid encoding an antibody that binds to Low-density lipoprotein receptor-related protein 5 (LRP5), wherein the antibody potentiates Norrin activity and/or Norrin/Fzd4 (Frizzled4) signaling, wherein the antibody comprises (a) HVR-H1 comprising the amino acid sequence GFTFSSYAMX$_1$, wherein X$_1$ is H or S (SEQ ID NO: 28), (b) HVR-H2 comprising the amino acid sequence GX$_1$ISX$_2$X$_3$GX$_4$STYYADSVKG, wherein X$_1$ is A or G, X$_2$ is A or S, X$_3$ is P or S, X$_4$ is S or W (SEQ ID NO: 26), or SRISSNGGSTYYADSVKG (SEQ ID NO: 27), (c) HVR-H3 comprising the amino acid sequence YYRYAPYRSLGMDV (SEQ ID NO: 23) or WIPQSYPFX$_1$SYKSGFDY, wherein X$_1$ is A or R (SEQ ID NO: 24), (d) HVR-L1 comprising the amino acid sequence RASQGISSYLA (SEQ ID NO: 29) or RASQX$_1$X$_2$X$_3$X$_4$YLA, wherein X$_1$ is A, G, S or V, X$_2$ is I or M, X$_3$ is F, G, S or Y, and X$_4$ is G, S or Y (SEQ ID NO: 30); (e) HVR-L2 comprising the amino acid sequence AASSLQS (SEQ ID NO: 31) or DASX$_1$X$_2$ES, wherein X$_1$ is S or T and X$_2$ is L or R (SEQ ID NO: 32); and (f) HVR-L3 comprising the amino acid sequence QQYYX$_1$YPFT, wherein X$_1$ is L or S (SEQ ID NO: 33).

2. The nucleic acid of claim 1, wherein the antibody comprises (a) HVR-H1 comprising the amino acid sequence GFTFSSYAMS (SEQ ID NO: 48), (b) HVR-H2 comprising the amino acid sequence GAISSSGSSTYYADSVKG (SEQ ID NO: 49), (c) HVR-H3 comprising the amino acid sequence YYRYAPYRSLGMDV (SEQ ID NO: 23), (d)

HVR-L1 comprising the amino acid sequence RASQGIS-SYLA (SEQ ID NO: 29); (e) HVR-L2 comprising the amino acid sequence AASSLQS (SEQ ID NO: 31); and (f) HVR-L3 comprising the amino acid sequence QQYYSYPFT (SEQ ID NO: 47).

3. The nucleic acid of claim 1, wherein the antibody comprises (a) HVR-H1 comprising the amino acid sequence GFTFSSYAMS (SEQ ID NO: 48), (b) HVR-H2 comprising the amino acid sequence GAISAPGSSTYYADSVKG (SEQ ID NO: 50), (c) HVR-H3 comprising the amino acid sequence YYRYAPYRSLGMDV (SEQ ID NO: 23), (d) HVR-L1 comprising the amino acid sequence RASQGIS-SYLA (SEQ ID NO: 29); (e) HVR-L2 comprising the amino acid sequence AASSLQS (SEQ ID NO: 31); and (f) HVR-L3 comprising the amino acid sequence QQYYSYPFT (SEQ ID NO: 47).

4. The nucleic acid of claim 1, wherein the antibody comprises (a) HVR-H1 comprising the amino acid sequence GFTFSSYAMS (SEQ ID NO: 48), (b) HVR-H2 comprising the amino acid sequence GAISSPGWSTYYADSVKG (SEQ ID NO: 51), (c) HVR-H3 comprising the amino acid sequence YYRYAPYRSLGMDV (SEQ ID NO: 23), (d) HVR-L1 comprising the amino acid sequence RASQGIS-SYLA (SEQ ID NO: 29); (e) HVR-L2 comprising the amino acid sequence AASSLQS (SEQ ID NO: 31); and (f) HVR-L3 comprising the amino acid sequence QQYYSYPFT (SEQ ID NO: 47).

5. The nucleic acid of claim 1, wherein the antibody comprises (a) HVR-H1 comprising the amino acid sequence GFTFSSYAMS (SEQ ID NO: 48), (b) HVR-H2 comprising the amino acid sequence GGISSPGSSTYYADSVKG (SEQ ID NO: 52), (c) HVR-H3 comprising the amino acid sequence YYRYAPYRSLGMDV (SEQ ID NO: 23), (d) HVR-L1 comprising the amino acid sequence RASQGIS-SYLA (SEQ ID NO: 29); (e) HVR-L2 comprising the amino acid sequence AASSLQS (SEQ ID NO: 31); and (f) HVR-L3 comprising the amino acid sequence QQYYLYPFT (SEQ ID NO: 53).

6. The nucleic acid of claim 1, wherein the antibody comprises (a) HVR-H1 comprising the amino acid sequence GFTFSSYAMH (SEQ ID NO: 43), (b) HVR-H2 comprising the amino acid sequence SRISSNGGSTYYADSVKG (SEQ ID NO: 27), (c) HVR-H3 comprising the amino acid sequence WIPQSYPFRSYKSGFDY (SEQ ID NO: 54), (d) HVR-L1 comprising the amino acid sequence RASQGIS-SYLA (SEQ ID NO: 29); (e) HVR-L2 comprising the amino acid sequence DASSLES (SEQ ID NO: 46); and (f) HVR-L3 comprising the amino acid sequence QQYYSYPFT (SEQ ID NO: 47).

7. The nucleic acid of claim 1, wherein the antibody comprises (a) HVR-H1 comprising the amino acid sequence GFTFSSYAMH (SEQ ID NO: 43), (b) HVR-H2 comprising the amino acid sequence SRISSNGGSTYYADSVKG (SEQ ID NO: 27), (c) HVR-H3 comprising the amino acid sequence WIPQSYPFASYKSGFDY (SEQ ID NO: 44), (d) HVR-L1 comprising the amino acid sequence RASQSI-YYYLA (SEQ ID NO: 55); (e) HVR-L2 comprising the amino acid sequence DASSLES (SEQ ID NO: 46); and (f) HVR-L3 comprising the amino acid sequence QQYYSYPFT (SEQ ID NO: 47).

8. The nucleic acid of claim 1, wherein the antibody comprises (a) HVR-H1 comprising the amino acid sequence GFTFSSYAMH (SEQ ID NO: 43), (b) HVR-H2 comprising the amino acid sequence SRISSNGGSTYYADSVKG (SEQ ID NO: 27), (c) HVR-H3 comprising the amino acid sequence WIPQSYPFASYKSGFDY (SEQ ID NO: 44), (d) HVR-L1 comprising the amino acid sequence RASQVI-YGYLA (SEQ ID NO: 56); (e) HVR-L2 comprising the amino acid sequence DASTRES (SEQ ID NO: 57); and (f) HVR-L3 comprising the amino acid sequence QQYYSYPFT (SEQ ID NO: 47).

9. The nucleic acid of claim 1, wherein the antibody comprises (a) HVR-H1 comprising the amino acid sequence GFTFSSYAMH (SEQ ID NO: 43), (b) HVR-H2 comprising the amino acid sequence SRISSNGGSTYYADSVKG (SEQ ID NO: 27), (c) HVR-H3 comprising the amino acid sequence WIPQSYPFASYKSGFDY (SEQ ID NO: 44), (d) HVR-L1 comprising the amino acid sequence RASQGI-FYYLA (SEQ ID NO: 58); (e) HVR-L2 comprising the amino acid sequence DASTLES (SEQ ID NO: 59); and (f) HVR-L3 comprising the amino acid sequence QQYYSYPFT (SEQ ID NO: 47).

10. The nucleic acid of claim 1, wherein the antibody comprises (a) HVR-H1 comprising the amino acid sequence GFTFSSYAMH (SEQ ID NO: 43), (b) HVR-H2 comprising the amino acid sequence SRISSNGGSTYYADSVKG (SEQ ID NO: 27), (c) HVR-H3 comprising the amino acid sequence WIPQSYPFASYKSGFDY (SEQ ID NO: 44), (d) HVR-L1 comprising the amino acid sequence RASQAI-YSYLA (SEQ ID NO: 60); (e) HVR-L2 comprising the amino acid sequence DASSLES (SEQ ID NO: 46); and (f) HVR-L3 comprising the amino acid sequence QQYYSYPFT (SEQ ID NO: 47).

11. The nucleic acid of claim 1, wherein the antibody comprises (a) HVR-H1 comprising the amino acid sequence GFTFSSYAMH (SEQ ID NO: 43), (b) HVR-H2 comprising the amino acid sequence SRISSNGGSTYYADSVKG (SEQ ID NO: 27), (c) HVR-H3 comprising the amino acid sequence WIPQSYPFASYKSGFDY (SEQ ID NO: 44), (d) HVR-L1 comprising the amino acid sequence RASQVM-GYYLA (SEQ ID NO: 45); (e) HVR-L2 comprising the amino acid sequence DASSLES (SEQ ID NO: 46); and (f) HVR-L3 comprising the amino acid sequence QQYYSYPFT (SEQ ID NO: 47).

12. The nucleic acid of claim 1, wherein the antibody comprises (a) HVR-H1 comprising the amino acid sequence GFTFSSYAMH (SEQ ID NO: 43), (b) HVR-H2 comprising the amino acid sequence SRISSNGGSTYYADSVKG (SEQ ID NO: 27), (c) HVR-H3 comprising the amino acid sequence WIPQSYPFASYKSGFDY (SEQ ID NO: 44), (d) HVR-L1 comprising the amino acid sequence RASQGIS-SYLA (SEQ ID NO: 29); (e) HVR-L2 comprising the amino acid sequence DASSLES (SEQ ID NO: 46); and (f) HVR-L3 comprising the amino acid sequence QQYYSYPFT (SEQ ID NO: 47).

13. The nucleic acid of claim 1, wherein the antibody is a monoclonal antibody.

14. The nucleic acid of claim 1, wherein the antibody is a human, humanized, or chimeric antibody.

15. The nucleic acid of claim 1, wherein the antibody is an antibody fragment that binds LRP5.

16. The nucleic acid of claim 1, wherein the antibody is a full length IgG1 antibody.

17. The nucleic acid of claim 1, wherein the antibody further comprises one or more heavy chain variable domain framework sequences selected from the group consisting of SEQ ID NO: 34-37.

18. An isolated nucleic acid encoding an antibody comprising a VH sequence of one of SEQ ID NOs: 1 to 11 and a VL sequence of one of SEQ ID NOs: 12 to 22.

19. The nucleic acid of claim 18, wherein the antibody comprises the VH sequence of SEQ ID NO: 1 and the VL sequence of SEQ ID NO: 12.

20. The nucleic acid of claim 18, wherein the antibody comprises the VH sequence of SEQ ID NO: 2 and the VL sequence of SEQ ID NO: 13.

21. The nucleic acid of claim 18, wherein the antibody comprises the VH sequence of SEQ ID NO: 3 and the VL sequence of SEQ ID NO: 14.

22. The nucleic acid of claim 18, wherein the antibody comprises the VH sequence of SEQ ID NO: 4 and the VL sequence of SEQ ID NO: 15.

23. The nucleic acid of claim 18, wherein the antibody comprises the VH sequence of SEQ ID NO: 5 and the VL sequence of SEQ ID NO: 16.

24. The nucleic acid of claim 18, wherein the antibody comprises the VH sequence of SEQ ID NO: 6 and the VL sequence of SEQ ID NO: 17.

25. The nucleic acid of claim 18, wherein the antibody comprises the VH sequence of SEQ ID NO: 7 and the VL sequence of SEQ ID NO: 18.

26. The nucleic acid of claim 18, wherein the antibody comprises the VH sequence of SEQ ID NO: 8 and the VL sequence of SEQ ID NO: 19.

27. The nucleic acid of claim 18, wherein the antibody comprises the VH sequence of SEQ ID NO: 9 and the VL sequence of SEQ ID NO: 20.

28. The nucleic acid of claim 18, wherein the antibody comprises the VH sequence of SEQ ID NO: 10 and the VL sequence of SEQ ID NO: 21.

29. The nucleic acid of claim 18, wherein the antibody comprises the VH sequence of SEQ ID NO: 11 and the VL sequence of SEQ ID NO: 22.

30. A host cell comprising the nucleic acid of claim 1 or 18.

31. A method of producing an antibody comprising culturing the host cell of claim 30 so that the antibody is produced.

* * * * *